United States Patent [19]
Cathcart et al.

[11] Patent Number: 5,443,791
[45] Date of Patent: Aug. 22, 1995

[54] AUTOMATED MOLECULAR BIOLOGY LABORATORY

[75] Inventors: G. Richard Cathcart, San Carlos; Thomas Brennan-Marquez, Sunnyvale; John A. Bridgham, Hillsborough; George S. Golda, El Granada; Harry A. Guiremand, Half Moon Bay; Marianne Hane, Burlingame; Louis B. Hoff, Belmont; Eric Lachenmeier, Cupertino; Melvyn N. Kronick, Palo Alto; Douglas H. Keith, Oakland; Paul E. Mayrand, Pacifica; Michael L. Metzker, San Bruno; William J. Mordan, Mountain View; Lincoln J. McBride, Belmont; John Shigeura, Fremont; Chen-Hanson Ting, San Mateo; Norman M. Whiteley, San Carlos, all of Calif.

[73] Assignee: Perkin Elmer - Applied Biosystems Division, Foster City, Calif.

[21] Appl. No.: 927,254

[22] Filed: Aug. 7, 1992

Related U.S. Application Data

[63] Continuation of Ser. No. 505,626, Apr. 6, 1990, abandoned.

[51] Int. Cl.⁶ .................. G01N 21/01; G01N 35/08; G01N 1/10; G01N 21/11
[52] U.S. Cl. .................. 422/65; 73/864.11; 73/864.25; 73/864.24; 364/188; 422/63; 422/67; 422/100; 422/104; 435/809; 436/54; 436/180; 436/526; 901/46
[58] Field of Search ........... 73/864.11, 864.24, 864.25; 215/247; 364/188; 137/846; 422/63, 65, 67, 99, 100, 102, 104, 106; 435/809, 296; 436/54, 180, 526; 901/46

[56] References Cited

U.S. PATENT DOCUMENTS 1,180,665  4/1916  McElroy ................. 215/247
2,579,724 12/1951  Breakstone ............. 215/247
3,754,444  8/1973  Ure et al. ............. 422/67 X (List continued on next page.)

FOREIGN PATENT DOCUMENTS 136126    4/1985  European Pat. Off. .
0209490   1/1987  European Pat. Off. ......... 436/526
63-195572 8/1988  Japan ..................... 422/100
8301912   6/1983  WIPO ..................... 422/100

OTHER PUBLICATIONS

Severns et al. "Pipette cleaning in automated systems" *J. of Automatic Chemistry* 1986, 8, 135–141.

(List continued on next page.)

Primary Examiner—James C. Housel
Assistant Examiner—Arlen Soderquist
Attorney, Agent, or Firm—Donald R. Boys; Joseph H. Smith

[57] ABSTRACT

A liquid-handling instrument has a worksurface with registration for modular stations to support containers of liquid, pipette apparatus with a pipette tip coupled to a sensing circuit, a robotic translation system for moving the pipette tip, and a control system with an iconic user interface for programming and editing. A gauge block registered on the worksurface provides for calibration using the sensing tip, and register cavities on the worksurface provide for modular stations. There is a wash station fop the pipette tip on the worksurface. An automated laboratory based on the liquid-handling system has heating and cooling and a sealable incubation station as well as a magnetic separation station. Methods are disclosed using the apparatus to convey droplets of liquid, to aspirate with minimum tip contamination, to mix liquids in containers, and to validate the worksurface. A duck-billed closure is disclosed for minimizing evaporation and cross-contamination during processing, and is a part of a container disclosed for storing and transporting liquids.

32 Claims, 26 Drawing Sheets

U.S. PATENT DOCUMENTS

| | | | |
|---|---|---|---|
| 4,134,512 | 1/1979 | Nugent | 215/247 |
| 4,224,278 | 9/1980 | Hogen Esch | 422/63 X |
| 4,326,851 | 4/1982 | Bello et al. | 422/100 X |
| 4,362,977 | 12/1982 | Evans et al. | 901/9 X |
| 4,422,151 | 12/1983 | Gilson | 73/864.25 X |
| 4,515,752 | 5/1985 | Miramanda | 422/102 X |
| 4,535,818 | 8/1985 | Duncan et al. | 137/846 |
| 4,539,855 | 9/1985 | Jacobs | 422/100 X |
| 4,566,493 | 1/1986 | Edwards et al. | 137/846 |
| 4,586,546 | 5/1986 | Mezei et al. | 73/864.24 X |
| 4,659,677 | 4/1987 | Glover et al. | 436/180 X |
| 4,730,631 | 3/1988 | Schwartz | 422/63 X |
| 4,818,492 | 4/1989 | Shimizu | 422/100 |
| 4,820,497 | 4/1989 | Howell | 422/63 |
| 4,869,114 | 9/1989 | Kido et al. | 73/864.24 |
| 4,895,650 | 1/1990 | Wang | 422/104 X |
| 4,897,244 | 1/1990 | Wallace et al. | 422/100 |
| 4,931,402 | 6/1990 | Abplanalp | 422/63 X |
| 4,963,493 | 10/1990 | Daftsios | 422/104 X |
| 4,969,993 | 11/1990 | Nash, Jr. et al. | 422/70 X |
| 5,027,075 | 6/1991 | Harding, Jr. | 73/864.24 X |
| 5,049,826 | 9/1991 | Sasao | 73/864.24 X |
| 5,061,630 | 10/1991 | Knopf et al. | 435/290 |

OTHER PUBLICATIONS

Wilson et al. "Automation of Dideoxynucleotide DNA Sequencing Reactions Using a Robotic Workstation" *BioTechniques,* 1988, 6, 776-787.

Connell et al. "Automated DNA Sequence Analysis" *BioTechniques,* 1987, 5, 342-348.

McBride et al. "A New, Reliable Cartridge for Rapid Purification of Synthetic DNA" *BioTechniques,* 1988, 6, 362-367.

Wilson, R K et al. Chemical Abstracts, vol. 109, 1988, abstract #223942d.

R. A. Zeineh *American Laboratory* 1976, 8, 51-53.

J. L. Guesdon et al. *Immunochemistry* 1977, 14, 443-447.

D. S. Ithakissios et al. *Clin. Chem.* 1977, 23, 2072-2079.

D. O. Kubiatowicz et al. *J. Nucl. Med.* 1978, 19, 854-857.

A. Wada et al. *Rev. Sci. Instrum.* 1983, 54, 1569-1572.

W. J. Martin et al. *Bio/Technology* 1985, 3, 911-915.

Vernay catalog Verney Laboratories, Inc Yellow Springs, Ohio.

W. J. Martin et al. *J. Phys. E: Sci. Instrum.* 1987, 20, 22-26.

R. Frank et al. *Bio/Technology* 1988, 6, 1211-1213.

J. Shigeura *Proc. 5th International Symp. Lab. Robotics* 1989 39-71.

U. Schröder et al, *Clin. Chem.* 1990, 36, 1282-1287.

```
|
|
|
52   ..........
53   ..........
54  : Open Lid
55    Lidopen?
56    ABORT "Lid Open Already"
57    Lid Locked?
58    ABORT "Lid Locked"
59    Lid Unlocked?  0=
60    ABORT "Lid Not Free"
61    Lid Close?  0=
62    IF BEGIN   KeyAbort
63         Locklid  Lid Close?
64       UNTIL
65       50 ms Kill
66   ...............
67   ...............
|
|
|
```

Fig. 2C

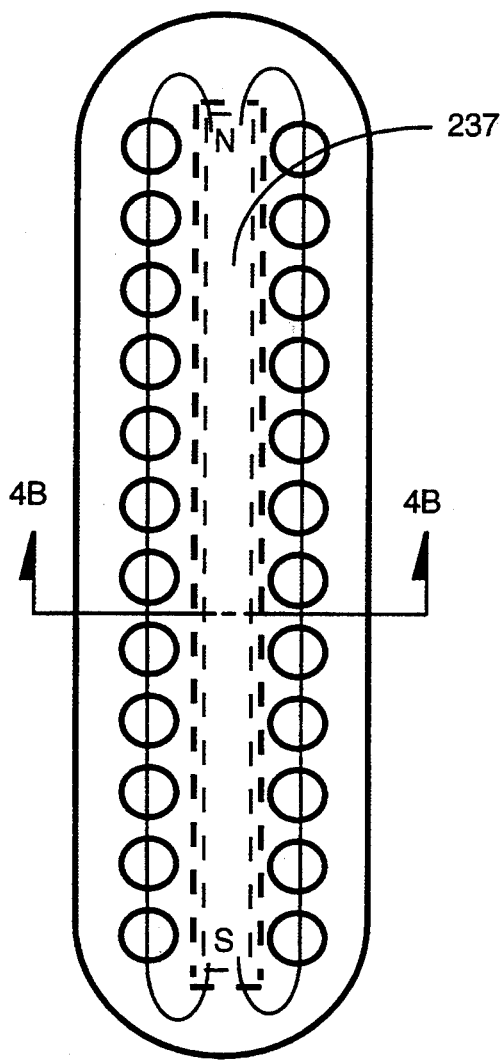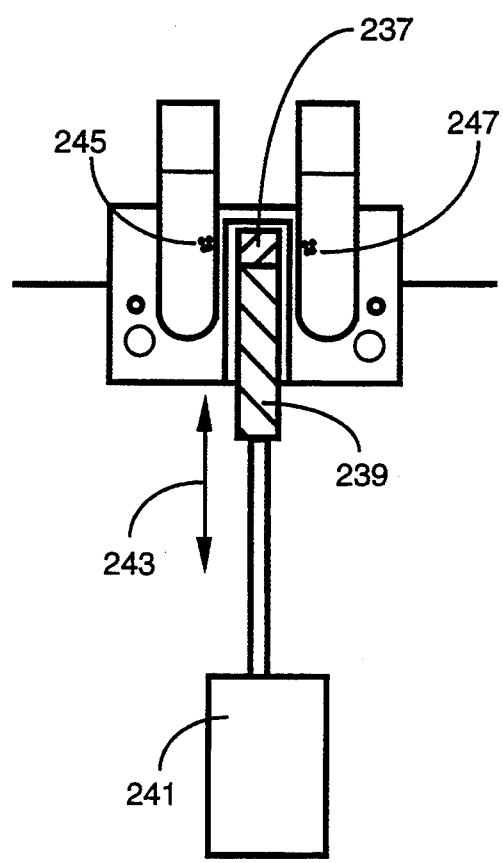
Fig. 4A
Fig. 4B

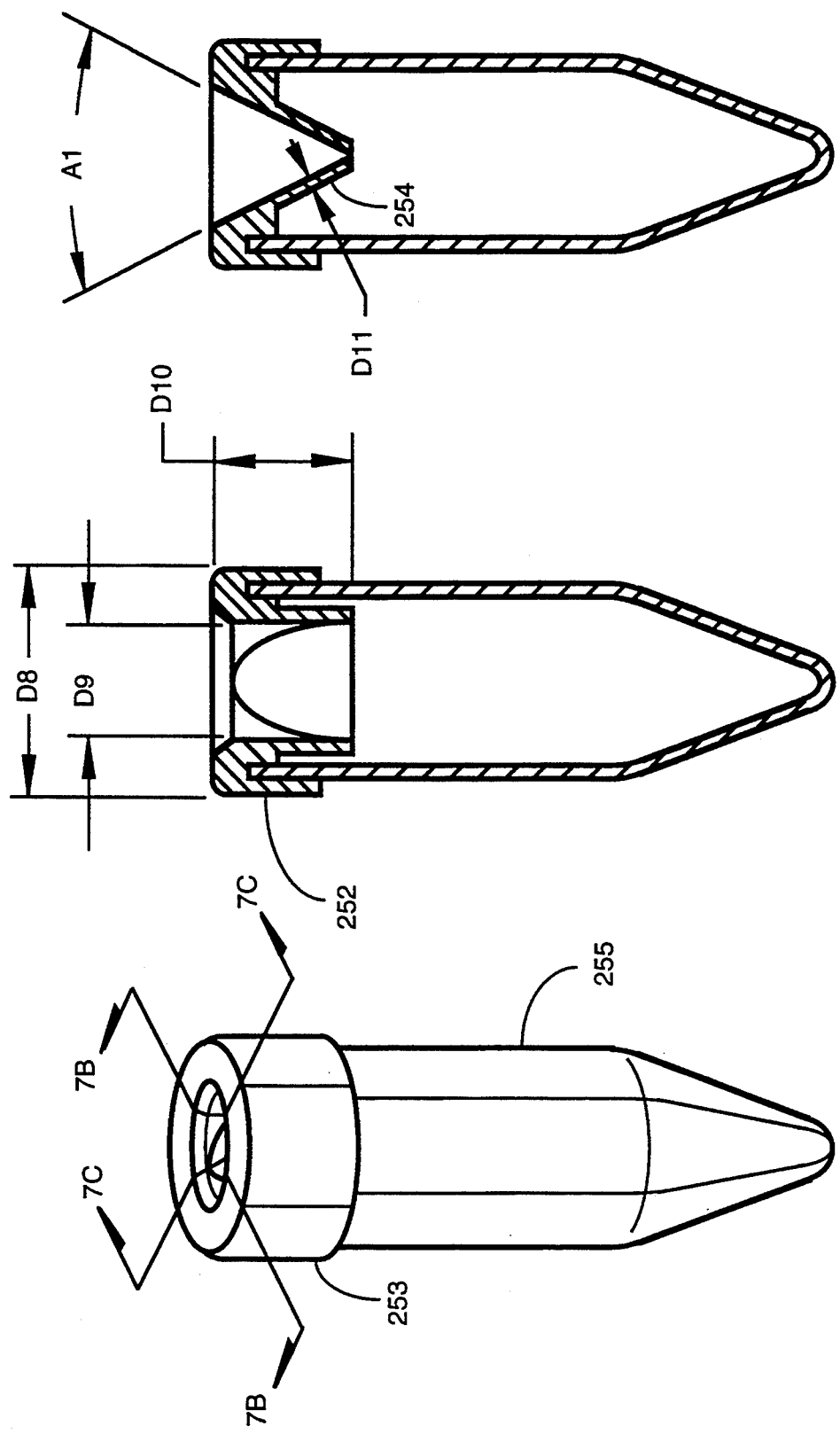

AUTOMATED MOLECULAR BIOLOGY LABORATORY

CROSS REFERENCE TO RELATED APPLICATIONS

This is a continuation of application Ser. No. 7/505,626, filed Apr. 4, 1990, now abandoned.

The present invention is related to application "ROBOTIC INTERFACE", Ser. No. 07/423,785, by Harry A, Guiremand, filed Nov. 17, 1989, which is hereby incorporated by reference.

FIELD OF THE INVENTION

The present invention is in the field of apparatus and methods for performing chemical studies and analyses and has particular application to chemistry protocols involving genetic material from samples of DNA.

BACKGROUND OF THE INVENTION

There has been rapid growth in recent years in apparatus and methodology for biochemical enterprise, particularly in the development of increasingly sophisticated systems for automating biochemical processes.

Procedures in chemistry, particularly in biochemistry, present generally more difficult problems for automation than many other kinds of processes and procedures. One reason is that there is often a very long sequence of steps in a biochemical procedure, such as gene detection and sequencing DNA. Another is that an automatic system needs to be very versatile, because different kinds of starting materials and different analytical purposes require different steps, different order of steps and the use of different kinds of chemical reagents. A third is that sample quantity is, for various reasons, quite limited, and only very small volumes, often on the order of microliters, must be used.

Systems have been designed to accomplish procedures useful in biochemical analysis, such as transfer of liquid from one container to another by pipette, and in general such systems mimic manual procedures. Typically a mechanical arm is moved over a limited area and carries one or more pipette tips. Systems of the prior art, however, have been mostly addressed to protocols in which liquid transfer is in volumes much larger then the microliter volumes often encountered in biochemical procedures, and these systems have been less than notably successful in addressing problems created by conditions such as those described above, like pipetting very small quantities of liquid with accuracy.

Aspirating liquid into and dispensing liquid from a pipette can be done several different ways. If a liquid is dispensed into air relatively rapidly, the liquid is dispensed at a regular rate, that is, in an analog fashion. If the same liquid is dispensed relatively slowly, the dispensing rate becomes, at some point, incremental. A droplet forms on the tip, grows, and separates from the tip, then another droplet grows and separates. The size of the droplet depends on such variables as the diameters and the design of the tip and the viscosity and surface tension of the liquid being dispensed. The viscosity and surface tension depend on other variables, among them the liquid material and the temperature.

The droplet phenomenon affects aspiration of liquid into a pipette from a container of liquid as well. Liquid is aspirated with a pipette below the surface of liquid in a container, but when the tip is withdrawn, a droplet can form on the tip, and affect the accuracy of the aspiration. The effect of the droplet size on accuracy depends on the volume to be aspirated and the droplet volume.

If a volume to be aspirated or dispensed is very large compared to the droplet size that forms on the pipette tip, the droplet phenomenon has little effect on accuracy. If, however, the amount to be aspirated or dispensed is in the range of, for example, ten times the volume of a single drop, the droplet phenomenon can be serious indeed, and accuracy may be seriously impaired. In the case of biochemical procedures, the sample size and the volume of material to be aspirated and dispensed is typically very small. If a liquid to be handled is quite viscous, such as genomic DNA for example, the droplet problem assumes larger proportions.

If liquid is to be dispensed into a container, and the container already contains liquid, the pipette tip can be submerged in the liquid in the container, much in the manner that liquid is typically aspirated, then additional liquid may be dispensed in an analog fashion. A new problem in this procedure, however, is that when the pipette is withdrawn from the liquid in the container, an uncontrolled amount of the liquid can adhere to the outside of the pipette and be carried away when the pipette is moved. Again, if the volume to be aspirated is large compared to the amount that adheres to the pipette, the inaccuracy is small. If the amount to be aspirated, however is small, as is typically the case in biochemical procedures, such as DNA sequencing, the amount that adheres to the outside of the pipette may introduce significant error. Also, the further a tip is immersed in a liquid whether aspirating or dispensing, the more liquid can adhere to the tip, and the greater may be the inaccuracy.

Another problem encountered is with the speed and precision of robotics. A robot for moving a pipette to accomplish liquid transfers from container to container is in some respects a simpler problem than manipulating solid objects. For example, a robot to do pipetting requires three degrees of freedom, while some robot devices require as many as seven. In biochemical procedures, however, it is generally necessary to access a large number of different sites, and to do so very accurately. It is desirable in gene detection and DNA sequencing, for example, to process a relatively large number of samples in a single procedure. To do so requires the addition of many different reagents for each sample, and the needed reagents are not in every case the same for each sample. There have to be sites in the scanned area of the robot arm for containers to hold all of the samples and for all of the necessary liquids to perform the procedures. Moreover, there is a need for other sites, such as a wash station for the pipette or pipettes and stations for such procedures as mixing, incubating, separating, and the like.

In the case of biochemical procedures, the number of sites and the lengthy procedures require that movement from site to site be accomplished quickly to save time. Moreover, the requirement for small volumes of samples and other liquids imposes a restriction of small containers, hence small targets for the pipette. Accuracy and resolution become more important for small targets.

Systems of the prior art mimic the manual processes of pipetting very poorly. A laboratory worker using a manual pipette develops detailed technique for pipetting liquids, and often employs such technique without considerable thought. For example, a worker will typically develop technique for approaching the surface of a liquid with a pipette tip very slowly, and will move the tip slowly and with precision at the liquid surface. A worker will also typically employ technique such as touching a droplet on the pipette to the surface of a liquid to transfer the droplet to the liquid mass. These movements made almost without conscious thought by a skilled worker are difficult to duplicate with a robot, and are typically not accomplished in automatic systems of the prior art.

Yet another problem encountered in automating biochemical procedures such as gene detection and DNA sequencing is associated with the systems of programming and control. It is known to operate such systems with computers and to program sequences of action for a computer to follow to accomplish the chemical procedures, but the large variation in steps, variation in variables such as heating, cooling and mixing, and the need to process a large number of samples at a time imposes a severe requirement for a system that is flexible and operator friendly, with an operator interface that is easy to use to set up process variations.

Still another problem encountered in the design of such a system is liquid integrity. Even with rapid movement of robotic components and short and compact site design, the large number of samples and large number of steps for each sample, coupled with time required for such things as heating and cooling, dictates that operations must be done over long periods, such as several hours. Given long processing times and small samples, evaporation can be a serious problem, and can cause significant uncontrolled changes in liquid concentration, introducing error. Moreover, open containers invite problems in cross-contamination. Such contamination can be from carryover with pipette operation and also from evaporation and condensation.

Another very serious problem with apparatus of the prior art is that such apparatus typically uses throw-away pipette tips, with a new tip being used for every pipette transfer. Such a system has to provide for discarding tips after use, a waste container to receive the discarded tips, storage for a large supply of fresh tips for use, and apparatus and control schemes for making the tip changes between liquid transfers. The apparatus and extra motions result in greater error than would result if a single tip could be used. Moreover, the need for discarding a tip and loading a new tip for each liquid transfer is time consuming, making the overall processing time more than would be necessary if a single tip could be used.

What is needed is automatic robotic apparatus for doing liquid transfers with very small quantities of liquids, and in a manner that avoids carryover and evaporation. Such an instrument needs to be modular in nature so that container stations may be interchanged, with modular stations for holding containers so that such operations as sample preparation and cleaning may be done off-line. Methods for operation of such apparatus are needed allowing a relatively large number of samples to be processed at a time, with samples and reagents placed in a close array to preserve space. The robotic actions need to be rapid to minimize overall processing time and extremely accurate to be able to access many small sites. Such a system also must incorporate robotic techniques to approximate human handling of pipette tips to accomplish adequate accuracy when operating with very small volumes of samples and reagents, and also when handling viscous liquids. The apparatus needs to provide a single pipette tip that can be reused to avoid the clumsy, time-consuming, and error-prone process of frequently discarding a tip and loading a new tip, and the problems of cross-contamination caused by single tip use must be addressed. The apparatus and associated methods of operation also must minimize evaporation and cross-contamination. Such an apparatus needs to be integrated with a control system that allows an operator to easily and quickly set up procedures with different variables, different step sequences, and different samples and reagents.

Also needed is laboratory apparatus based on such a liquid handling system to incorporate further techniques, such as temperature control and a separation station, to be able to fully automate specific chemistry protocols such as for gene detection and DNA sample purification.

SUMMARY OF THE INVENTION

In accordance with the preferred embodiments of the present invention there is provided a liquid-handling instrument, to transfer liquid between containers supported on a worksurface. The instrument has a pipette system for aspirating and dispensing liquid and a robotic translation system for moving the tip of the pipette into and out of the containers. There is a washing device for washing the pipette tip between transfers of liquid to avoid cross-contamination and a control system for programming steps for liquid transfers and for controlling the instrument. The pipette system has a sensing system to sense and communicate proximity of the tip to surfaces on the instrument to the control system. In one embodiment the sensing system has a conductive tip connected to a capacitance sensor. The sensing feature lets the robotic system move the tip with the precision needed for aspirating and dispensing very small volumes of liquid.

In another embodiment there is a gaugeblock registered to the worksurface for use in calibrating the control system relative to a precise position on the worksurface. The worksurface also has registration cavities so modular stations may be substituted on the worksurface without losing position integrity, which provides for cleaning and sample setup off-line.

The instrument has two syringe pumps connected to the common tip, and the pumps have different capacities, so course and fine aspirations and dispenses may be made with the same tip.

The robot in an embodiment is a cartesian device driven by electrical drives with two directions of travel in a horizontal plane over the worksurface and a third at right angles to the surface. The control system has an iconic, user-friendly interface for a user to program steps and enter and edit variable values. The icons are arranged in a manner that more primitive icons are nested in higher-order icons such that higher-order icons can be expanded-in-place to show more program detail without losing relationship with position in a program.

A duck-billed closure is disclosed for closing a container to minimize exposure of liquid in the container while allowing easy access by a needle-like device. A liquid-handling instrument according to the invention uses containers with the duck-billed closures to help prevent cross-contamination and evaporation. A container with a duck-billed closure is also disclosed for storing and transporting liquids.

An automated laboratory of the present invention for performing chemistry protocols is based on the liquid-handling instrument and has heating and cooling systems to control temperature of samples and reagents during processing. The laboratory has a heated and cooled incubation station with coated container cavities and a latching, sealing lid for sealing container cavities while incubating. The laboratory also has a magnetic station for separating paramagnetic particles from liquids, and the magnetic station has a magnet bar moveable vertically between rows of containers of liquid.

A method is also provided to transfer discrete droplets of liquid, and another method is provided to aspirate small volumes of liquid while minimizing tip contamination. Yet another method is provided to mix liquids effeciently with apparatus according to the preferred embodiments. Still another method is provided for validating the placement of elements on a worksurface of the present invention.

BRIEF DESCRIPTION OF THE DRAWINGS

FIG. 2C is an example of a partial script list as used in the control system.

FIG. 4A is a plan view of a magnetic station.

FIG. 4B is an elevation view in section of the plan view of FIG. 4A with a magnet extended.

FIG. 7A is a perspective view of an assembly of a duck-billed closure to a container.

FIG. 7B is a section through the assembly of FIG. 7A.

FIG. 7C is another section through the assembly of FIG. 7A at right angles to the section of FIG. 7B.

DESCRIPTION OF THE PREFERRED EMBODIMENTS

General Description

Figure 1:
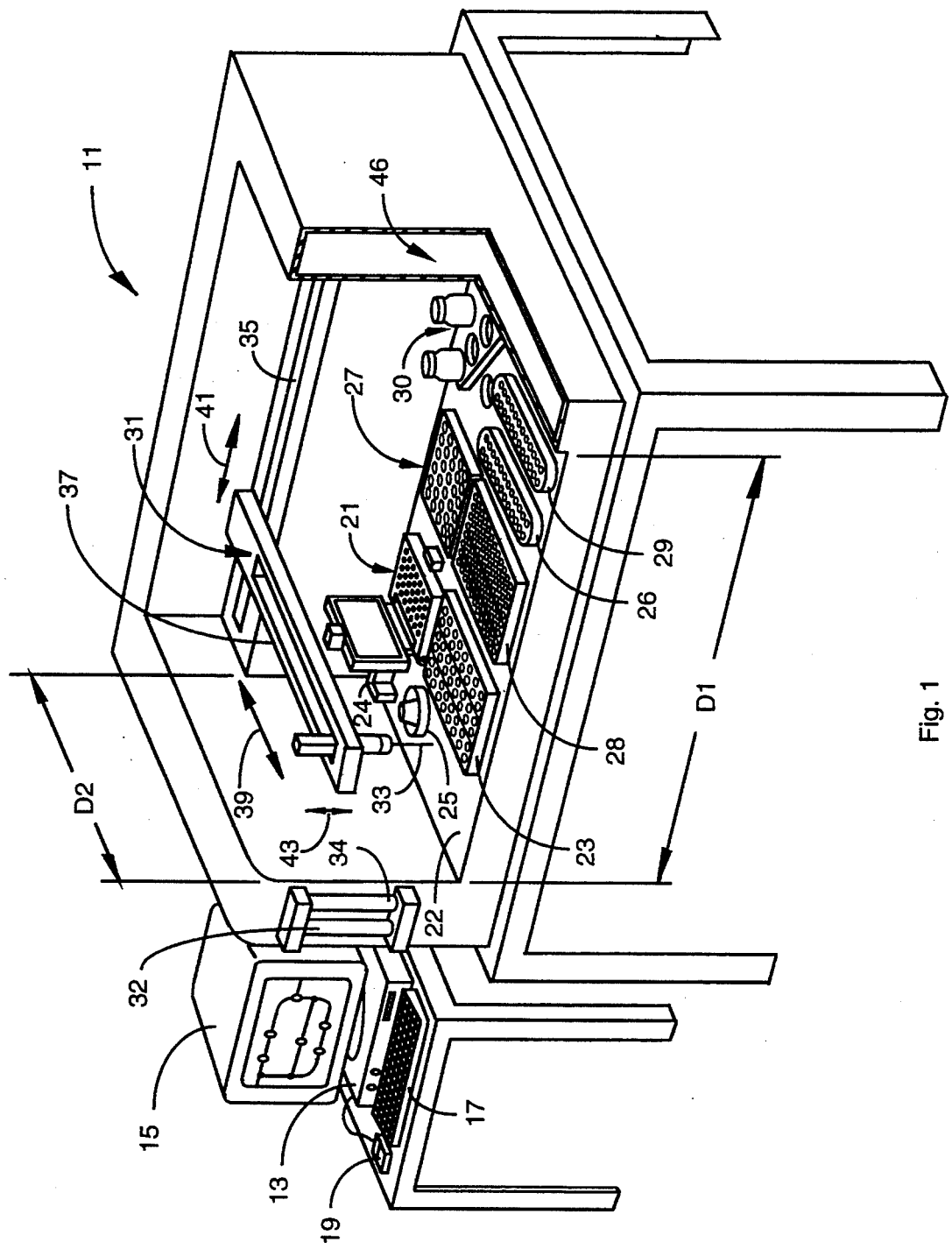
FIG. 1 is a perspective view of an automated laboratory according to a preferred embodiment of the invention.

FIG. 1 is a perspective view of a preferred embodiment of an automated laboratory (AL) 11 for performing chemical processes involved in molecular biology. A computer 13 with a CRT monitor 15, a keyboard 17 and a mouse device 19 is connected to the AL. The computer, CRT display, mouse, and keyboard are hardware components of a control system with an operator interface for programming the AL to perform sequences of activities, for starting and stopping processes and sequences of processes and for entering and altering process variables for specific activities. In the preferred embodiment the computer is a Macintosh II CX computer made by Apple Computer of Cupertino, Calif., but other computers may also be used.

In a preferred embodiment of the invention for performing DNA sequencing the AL has a closeable, heated, clamped-lid thermal cycling station 21, an actively cooled enzyme storage station 23, a wash station 25, a reagent storage position 27 for storing and presenting frequently used reagents, a DNA sample stage 28, a wash buffer storage 30, and two magnetic particle wash stations 26 and 29 for manipulating paramagnetic particles in suspension in liquid mixtures. Also shown is a gauge block 24 for use in calibrating the robotic drives for the apparatus. The various stations are arranged on a worksurface 22. Width D1 of the worksurface where all of the stations are arranged is about 50 cm and depth D2 is about 35 cm. The height is about 17 cm. In the preferred embodiment the stations on the worksurface are registered in cavities machined into the worksurface maintaining close tolerance dimensions from cavity to cavity and to the position of the gauge block, so modular stations may be interchanged while maintaining information about the position of containers relative to the worksurface and the gaugeblock.

The magnetic particle wash stations shown are not required for the DNA sequencing protocol included in the description of the preferred embodiment, but are useful for other chemistries and illustrate the flexibility of the apparatus and to provide for ability to do chemistry protocols other than the DNA mentioned above. For example, a projected use of the apparatus of the invention is in purification of biological samples, and the magnetic particle wash stations would be used. A portion of the AL at region 46 is shown cut away to better illustrate the components in the work area.

Thermal cycling station 21 has a 96 position array of reaction cavities in 8 columns and 12 rows. The representation in FIG. 1 does not show 96 stations for reasons of detail, and the number 96 is convenient, as it is compatible with the 96 well Microliter plate known and used in the industry. There can be more or fewer reaction cavities. The reaction cavities are machined into an aluminum plate that is electrically resistance heated and also has internal water cooling passages and a thermal sensor for feedback control. Temperature is controlled in the range from 4 degrees C. to 100 degrees C. in the preferred embodiment with 1 degree C. per second rate of change. The reaction cavities are coated with Paralene (TM), a largely chemically inert coating for which materials and process are available from Solid Photography, Inc. of Melville, N.Y.

A hinged lid has a polymer undersurface such that, when the lid is closed, the reaction cavities are sealed. Each reaction cavity has a machined detail ring to contact the polymer undersurface to effect sealing (see element 285, FIG. 12). The lid is closable automatically and held closed by a latch in the preferred embodiment. Clamping by the latch is necessary to effect an adequate seal on the seal ring. Various kinds of lid drives, such as motor and pneumatic drives are useful, and various kinds of latches may be used, such as mechanical or magnetic. Sealing prevents evaporations which helps to preserve liquid volume integrity and prevent vapor cross-contamination.

Enzyme storage station 23 has three 2 by 8 position arrays for 1.5 mL screw-top tubes, such as available from Sordstadt. The block at station 23 has cooling passages for maintaining temperature of stored enzymes at 4 degrees C. with a tolerance of 1 degree C. Although not shown in FIG. 1, a top closure is provided for station 23 with holes in the same array as the 48 tube positions, and the holes are slightly larger in diameter than the pipette tip. The top closure helps to maintain the lower temperature desirable for enzyme storage and holds the tubes in place.

Wash station 25 is for washing the pipette tip between liquid transfers to avoid carryover type cross-contamination. The wash station is connected to a waste drain and serves also as a disposal station for liquids that must be expelled from a pipette in a process protocol.

Reagent storage position 27 has positions for 1.5 mL screw-top tubes and has no active heating or cooling. The number of positions is optional. Typically 48 positions are provided.

DNA sample stage 28 has 96 positions in an 8 by 12 array for tubes containing DNA samples, also with no active heating or cooling.

Magnetic particle wash stations 26 and 29 each have a 2 by 12 array for 1.5 mL microtubes, and station 26 has active heating and cooling, similar to station 21. Each magnetic station has a three-position vertically moving magnet. The magnets are for manipulating paramagnetic particles used in various protocols to capture specific material from solution.

Wash buffer storage station 30 has positions for storage containers for buffer storage. Active heating is provided with temperature sensing and control.

A cartesian transport apparatus 31 moves a pipette needle 33 of a system for aspirating liquids from containers at the various stations and dispensing liquids at the same or other stations. The pipette system includes two motor-driven syringe pumps 32 and 34 in the preferred embodiment. Pump 32 is for relatively course transfer, and pump 34 is for transfer of precise amounts of liquids. Typically pump 32 has a larger capacity than pump 34, and the capacity varies depending on the application. For example, pump 32 can vary from 250 microliter capacity for some protocols to 5 milliliters for others, and pump 34 typically has a capacity from 50 to 100 times smaller than pump 34. The two syringes have a common source of diluent. In the preferred embodiment TFE tubing is used from the syringes to the pipette probe tip, with an internal volume of 1.1 mL. The probe is fitted with a highly polished stainless steel tip that can convey about 5 microliter maximum droplet size.

The probe tip in the preferred embodiment is made part of a sensing system for determining when the tip approaches or touches a surface. The tip is conductive, and a wire from a capacitance sensing device is connected to a an electrical contact that contacts the probe tip. A signal is provided to the control system whenever the tip contacts a surface on the AL, and with appropriate circuitry, known in the art, proximity to a surface may also be detected without actually touching. One use of the capacitance sensing tip is to sense the surface of liquids when positioning the tip for liquid transfer operations. By sensing a liquid surface and at the same time keeping track of the height of the tip relative to the worksurface, the liquid level, hence the volume of liquid in a container can be determined. Sensing a liquid surface also provides information as to when and where to aspirate and dispense liquid while minimizing tip contamination.

Another use for the sensing tip is to examine the physical nature of the working area over which the sensing tip may pass. By passing the tip over the working area at a pre-determined height, at which height the tip will encounter no obstacle if all parts are in their proper place, one can validate the working area. If the tip encounters a surface at any place a surface should not be encountered, it is known that there is a part out of position. The control system can be programmed to provide a warning in any such circumstance.

Transport device 31 moves along slot 35 passing over the storage and activity stations. The pipette needle is movable along arm 37 of the transport device in the direction of arrow 39 and the transport is movable along slot 35 in the direction of arrow 41 to position the pipette over any container position at any station. The pipette needle is translatable vertically in the direction of arrow 43 so the transport apparatus is a cartesian XYZ mechanism capable of placing the pipette in any container on the AL work surface.

A gauge block 24 in one corner of the work area is used for calibrating the control system as to position of the pipette tip. The gauge block and the active sites on the work area are all registered to the worksurface with accurate known dimensions. The stations on the worksurface are modular in this fashion, such that a station can be easily and quickly removed and another put in its place, or one kind of station may be substituted for another on the worksurface. Making the stations modular and providing accurate registration to the worksurface allows accurate calibration of the robotic elements to workstation positions at all times.

The gauge block has a machined surface for each of the three directions of movement of the cartesian robot, and by approaching and sensing each of the three surfaces in turn with the capacitance sensing probe tip, an accurate home position is communicated to the control system at the start of each protocol in the preferred embodiment. The probe tip can be used in the same way to validate positions of stations and elements on the worksurface. As an example, if a tube at a particular site is wedged out of position in a register opening, such as at too great a height above the worksurfaces the probe with capacitance sensing can be used to determine that fact and communicate it to the control, which may then signal for appropriate action.

The pipette is for aspirating liquid from any one container and dispensing it into any another container. With the pipette, mixtures of various liquids are made and transported to any other container on the AL. The pipette system also serves to agitate liquids in a container to accomplish mixing, by repeated aspirating and dispensing of the liquid in a container, and in some instances by programmed movement of the tip in concert with aspiration and dispensing. Wash station 25 is for washing the pipette tip to avoid cross-contamination.

Computer 13, CRT 15, mouse 19 and keyboard 17 are used with the ROBOTIC INTERFACE referenced earlier, which is a unique iconic program, hereinafter called Popframes, to prepare control sequences and establish specific characteristics for the various activities that make up a complete control sequence, as well as to initiate and terminate specific strings of activities. Entries are also made at the computer to relate specific positions at specific stations on the worksurface with specific samples, such as DNA samples, and with specific reagents that are to be stored at specific sites. The iconic control program is described in further detail in another portion of this specification titled "ROBOTIC INTERFACE".

Control Functions

Figure 2A:
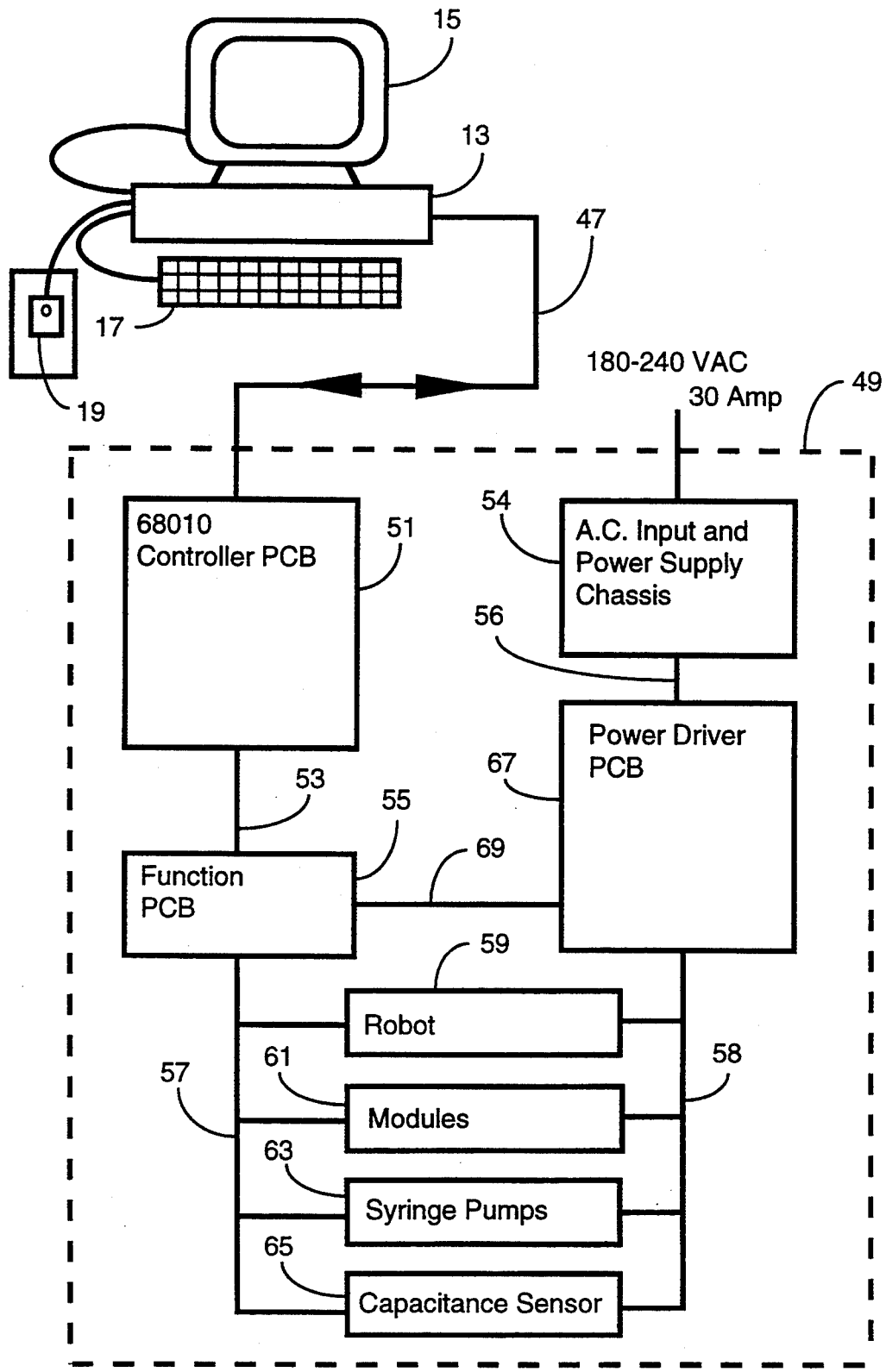
FIG. 2A is a schematic representation of hardware components of a control system in a preferred embodiment.

FIG. 2A is a block diagram showing control activities and modules in the preferred embodiment. There are many other control configurations that could be used. Computer 13, keyboard 17, mouse 19, and display 15 are connected together in the usual way, and the computer is connected by communication line 47 to a Motorola 68010 Controller PCB 51 located within the AL chassis represented by dotted enclosure 49.

Controller PCB 51 accomplishes high level control functions, such as calculations of robot position and interpretation of communication from the computer, and translation of the computer communication into more fundamental control signals for other control hardware.

The controller PCB communicates by path 53 with Function PCB 55. The function PCB accomplishes, among other functions, all of the Input/Output (I/O) operations necessary in the control operations. There are, for example, sensors on the AL to sense positions of the robot arm, such as mechanical switches. For practical reasons the sensors are operated with AC power and at a higher voltage than could be tolerated by the computer. The Function PCB monitors the status of position sensors as digital data and converts that data to computer level signals for the computer part of the control system.

In addition to the digital IO data described above, the Function PCB monitors analog data communicated by analog sensors on the AL, such as temperature monitoring sensors. The Function PCB converts the analog data to data suitable for the computer portion of the control system. The Function PCB handles all analog-to-digital (A/D) conversion and digital-to-analog (D/A) conversion between the computer portion and actuators and other equipment on the AL.

Function PCB 55 communicates along path 57 with the X-Y-Z robot 59, the station modules 61 on the worksurface, the syringe pumps 63 and the capacitance sensor probe 65, and also with Power Driver PCB 67 through path 69. Communications along path 57 are primarily sensol data sent to the Function PCB. Signals along path 69 are primarily signals from the Function PCB to the Power Driver PCB to actuate motions on the AL.

An AC Input and Power Supply chassis 54 in the AL receives primary AC power from outside the AL, and has the purpose of dividing, conditioning, and providing power to all the power requirements on the AL, which it does by virtue of on-board power supplies connected to the Power Driver PCB along path 56. The Power Driver PCB has the primary function in the preferred embodiment of switching power to various drivers on the PCB as required for operation, such as to the DC motors that operate the X, Y, and Z motions of the robot. The power to the various parts of the AL is provided primarily along path 58.

Figure 2B:
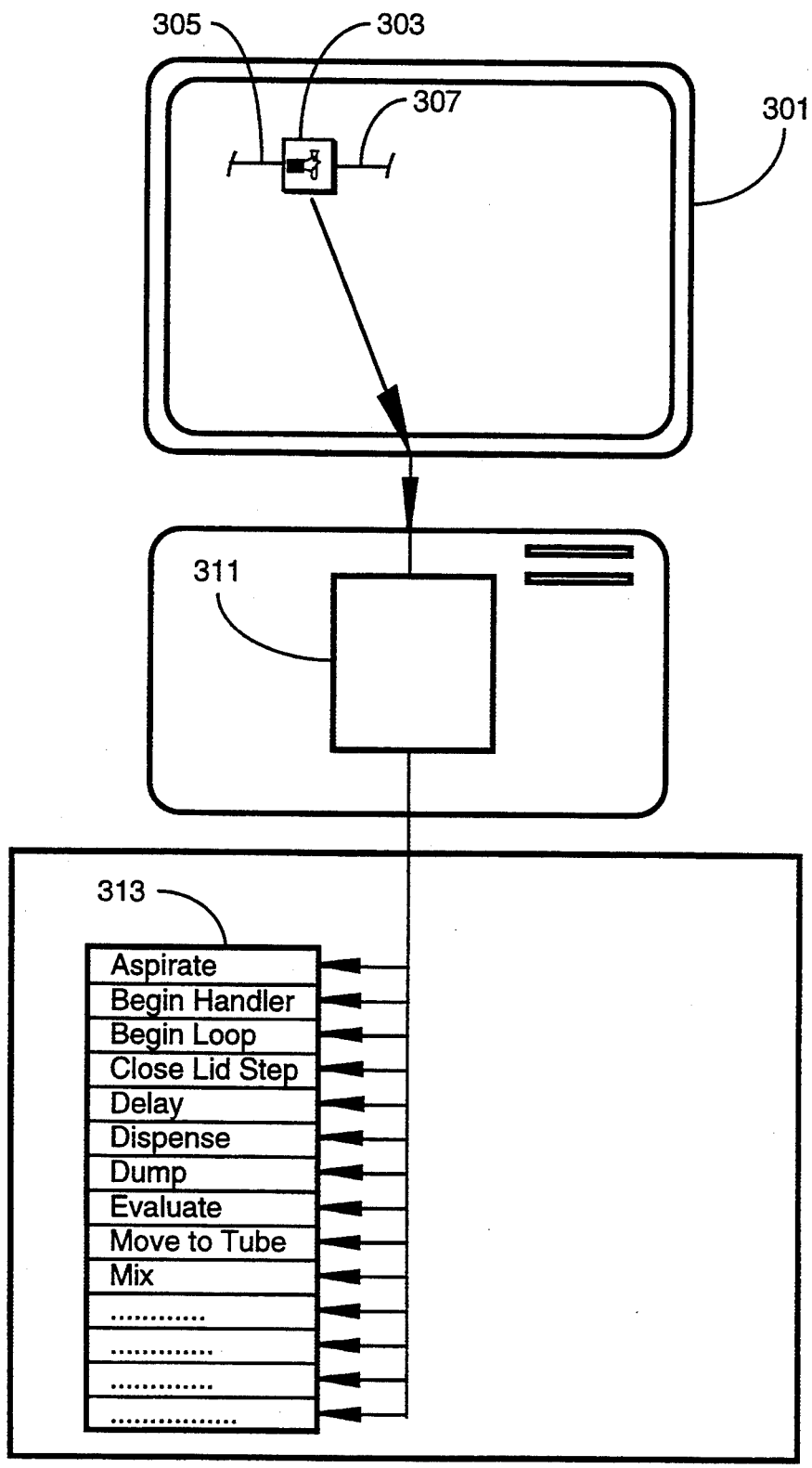
FIG. 2B is a schematic representation to illustrate hardware and software structure for a control system in a preferred embodiment.

FIG. 2B is a largely schematic drawing to illustrate in greater detail how communication passes from the computer, a Macintosh II CX in the preferred embodiment, to other control hardware, and to illustrate in more detail the structure of software for accomplishing the tasks. As mentioned above, and described in more detail below, the interface for setup of the AL regarding constants and variable values, and for programming protocols, is an iconic program called Popframes.

In Popframes, a high level sequence of more basic steps is indicated on monitor 301 of the control computer by an icon such as icon 303. The lines 305 and 307 extending from the icon indicate sequential connection to other icons in a programmed protocol, although other such icons are not shown in FIG. 2B.

Each icon developed for Popframes is associated with a command list called a script, and the script for icon 303 is represented in FIG. 2B by enclosure 311. When an icon is activated, as in sequential performance of a series of icons to perform a protocol, the script for the icon is called in the Macintosh hardware. The script is sent to the Motorola 68010 PCB in the AL chassis in the preferred embodiment. FIG. 2C is a short excerpt from a script list. Script is programming protocol available from Apple Computer of Cupertino, Calif. and used with Apple computer hardware.

The script sent to the Motorola 68010 microprocessor in the preferred embodiment is interpreted there into Forth protocols that are themselves lists of more primitive functions for the AL. For each script step there is a Forth kernel programmed on the 68010, and kernel list 313 shows a selected few of the kernels. Each script step activates a Forth kernel, and a series of primitives is performed in an order often determined by setting of flags and other variables. Communication from the Forth kernels to discrete actuators on the AL is not shown in FIG. 2B. Forth is a well known language often used in the art to program controls for robotic devices, and there are many reference books in the art explaining the structure and use of Forth.

Figure 2D:
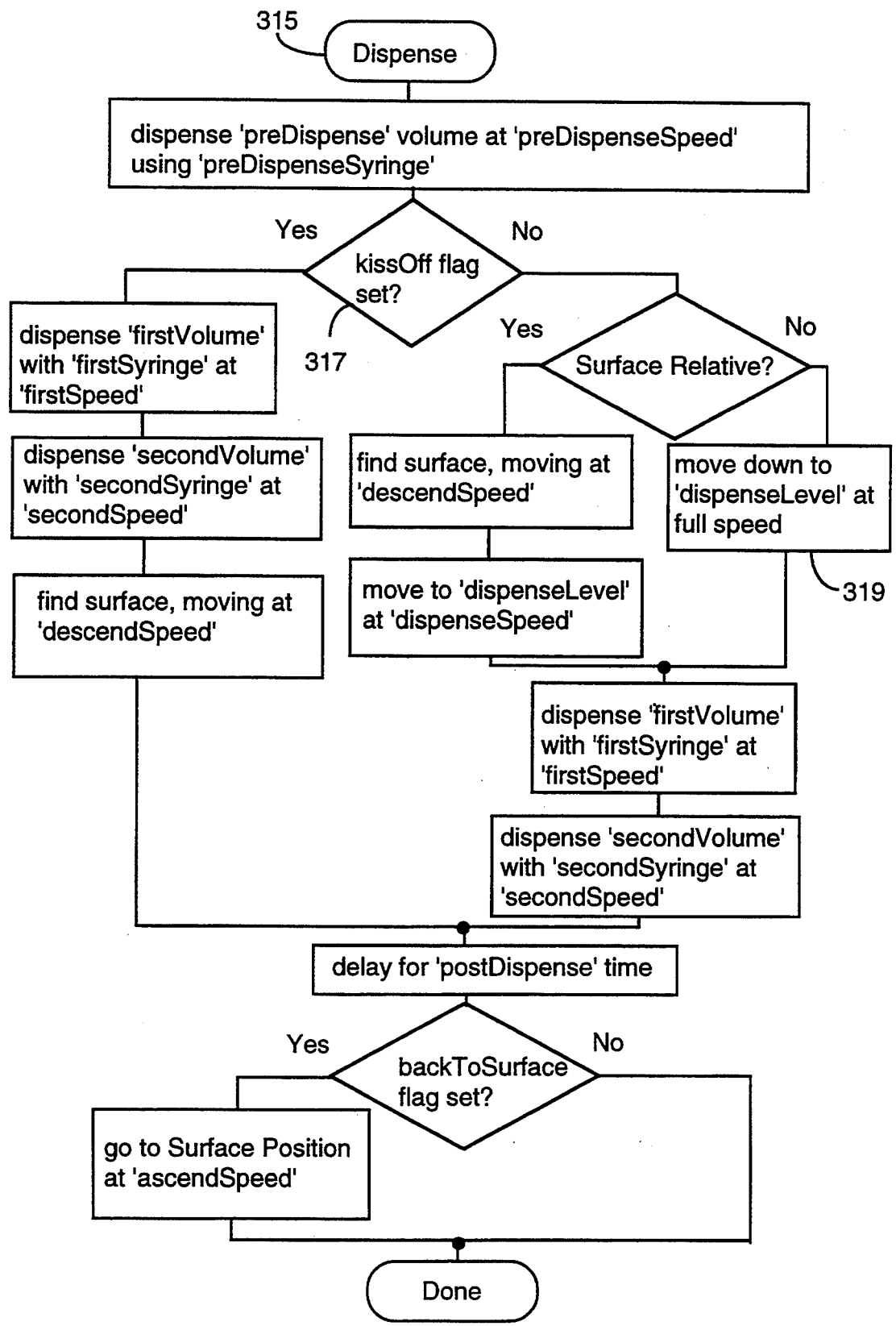
FIG. 2D is a flow diagram showing the flow of primitives for a specific script command called Dispense.

FIG. 2D is a flow diagram showing a sequence of more primitive functions associated with one script step called Dispense, which controls dispensing of liquid from the pipette tip. Element 315, the Dispense Script command is the start of the sequence, and there are several decision points, based upon flags that can be set. One such is decision point 317, asking if the KissOff flag is set. If the flag is set, the procedure follows one path, and if not, another path is followed.

Within the sequence for Dispense the expressions enclosed in single quotes are values stored in memory that the software accesses and uses to actuate specific functions for which there may be a choice. 'descendSpeed' for example is a rate of travel for the system to use to move the pipette tip downward toward a liquid surface. As in common in the Forth language, many of the primitives are themselves combinations of even more basic functions. For example, element 319, "move down to 'dispenseLevel' at full speed is composed of a sequence that starts the vertical drive, ramps it up to full speed (pre-programmed), ramps it down near the 'dispenseLevel', and stops the drive with the pipette tip at 'dispenseLevel'.

The Cartesian Robot

Figure 3A:
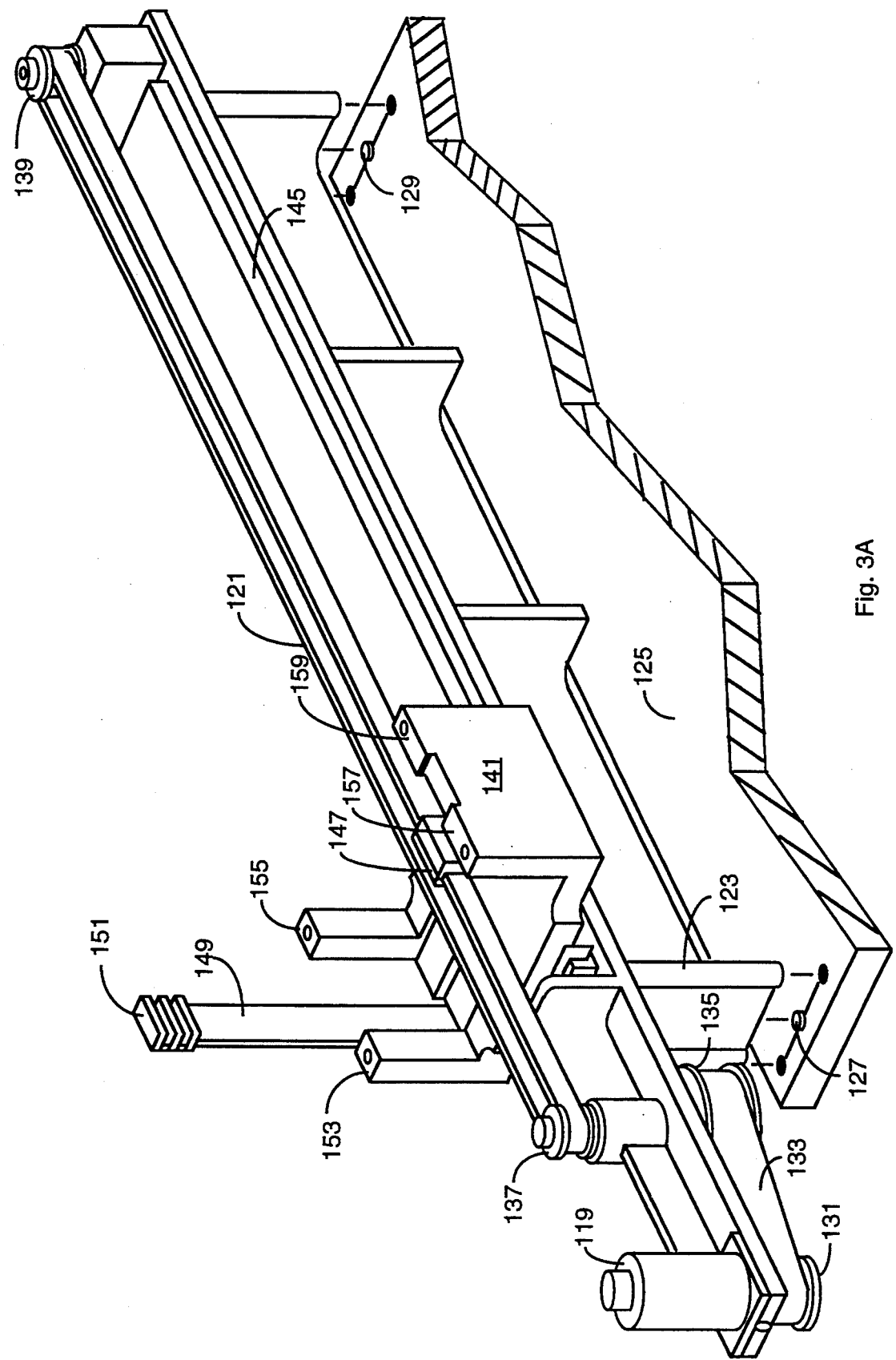
FIG. 3A is a perspective view of a robotic arm assembly for movement in the horizontal plane.

FIG. 3A is a perspective view of mechanisms for driving cartesian robot 31 in the X-direction, which is the direction of arrow 41 in FIG. 1. The view of FIG. 3A has the Y-direction and Z-direction mechanisms removed, so the X-direction mechanisms may be better illustrated.

X-direction motion is provided by a D.C motor 119 that drives a flexible gear belt 121. A cast frame 123 supports the X-direction drive assembly, and the frame is mounted by conventional fasteners to baseplate 125, which is the baseplate to which stations on the worksurface in FIG. 1 are mounted. The frame is positioned precisely on the baseplate by locator pins, such as pins 127 and 129.

Motor 119 is mounted to frame 123, and a pully 131 on the motor shaft drives an intermediate toothed gear belt 133 which in turn drives another pulley 135. Pully 135 is mounted on a shaft through frame 123 in bearings (not shown) and drives yet another pulley 137. Gear belt 121 extends between driven pulley 137 and an idler pulley 139 at a distance greater than the maximum X-direction movement, which is about 45 cm. in the preferred embodiment.

A travelling cast carriage 141 is mounted below gear belt 121 on linear bearings arranged such that the carriage rides on a linear guide bar 145, which is fastened also to frame 123. Carriage 141 is attached to one side of gear belt 121 by a clamp 147 such that, as motor 119 causes belt 121 to traverse, the carriage is caused to traverse along bar 145 in the X-direction.

Extension 149 from carriage 141 carries optical sensors 151 for sensing flags (not shown) fastened to the AL frame to signal position to the AL control system. The linear bearings are precision bearings such that the maximum runout from end-to-end does not exceed about 0.005 inches (0.013 cm).

A serious problem with previous cartesian mechanisms for liquid transfers for chemistry protocols is that the resolution and repeatability has not been sufficient for accurate probe tip placement in small vials and at closely arrayed reaction cavity positions. In the present invention, the reaction cavities, for example, at station 21 (FIG. 1) are on about 1 cm centers, and the diameter of each cavity at the base is about 0.12 cm. The shaft encoders and bearings used for the X-drive, along with the control system, provide resolution of the robot in the X-direction of 0.020 mm.

Figure 3B:
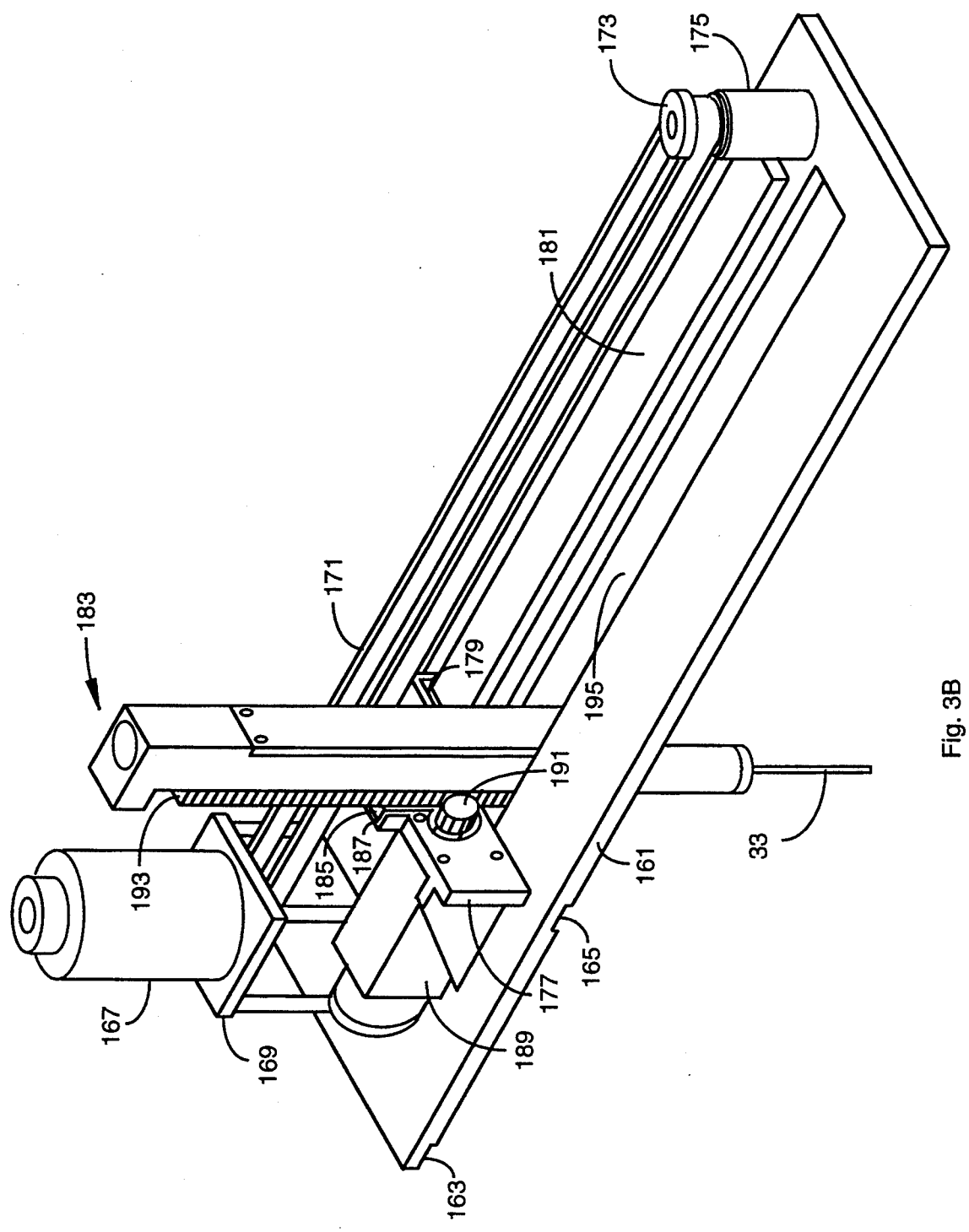
FIG. 3B is a perspective view of a robotic arm assembly also for movement in the horizontal plane, but at right angles to the movement of the arm of FIG. 3A.

Lands 153, 155, 157 and 159 on carriage 141 are machined at a constant height to mount mechanism for Y-direction translation. FIG. 3B shows the Y-direction mechanisms. In FIG. 3B, base plate 161 is the frame for mounting other components, and plate 161 mounts to carriage 141 of FIG. 3A and travels with that carriage. Surface 163 mounts to land 153 of FIG. 3A and surface 165 mounts to land 157 of FIG. 3A. The surfaces that mount to lands 155 and 159 on carriage 141 are not seen in FIG. 3B. Mounting plate 161 is shown as a flat plate for simplicity, but is typically a casting with reinforcement ribs and the like in the preferred embodiment.

Y-drive motion is provided by a D.C. drive motor 167 mounted to a stand 169, that is fastened to plate 161. The motor drives a pulley (not shown) on the motor shaft, which drives a gear belt 171 around an idler pulley 173 rotatably mounted to a standoff 175 near the end of plate 161 opposite the end where the drive motor is mounted. A moving carriage 177 is mounted on linear bearing 179 and constrained to guide along a guide bar 181 affixed to plate 161. Carriage 177 is fastened to belt 171 by a clamp (not shown) similar to clamp 147 of FIG. 3A, such that as motor 167 turns and belt 171 is driven, carriage 177 moves along guide bar 181 in the Y-direction.

Figure 3C:
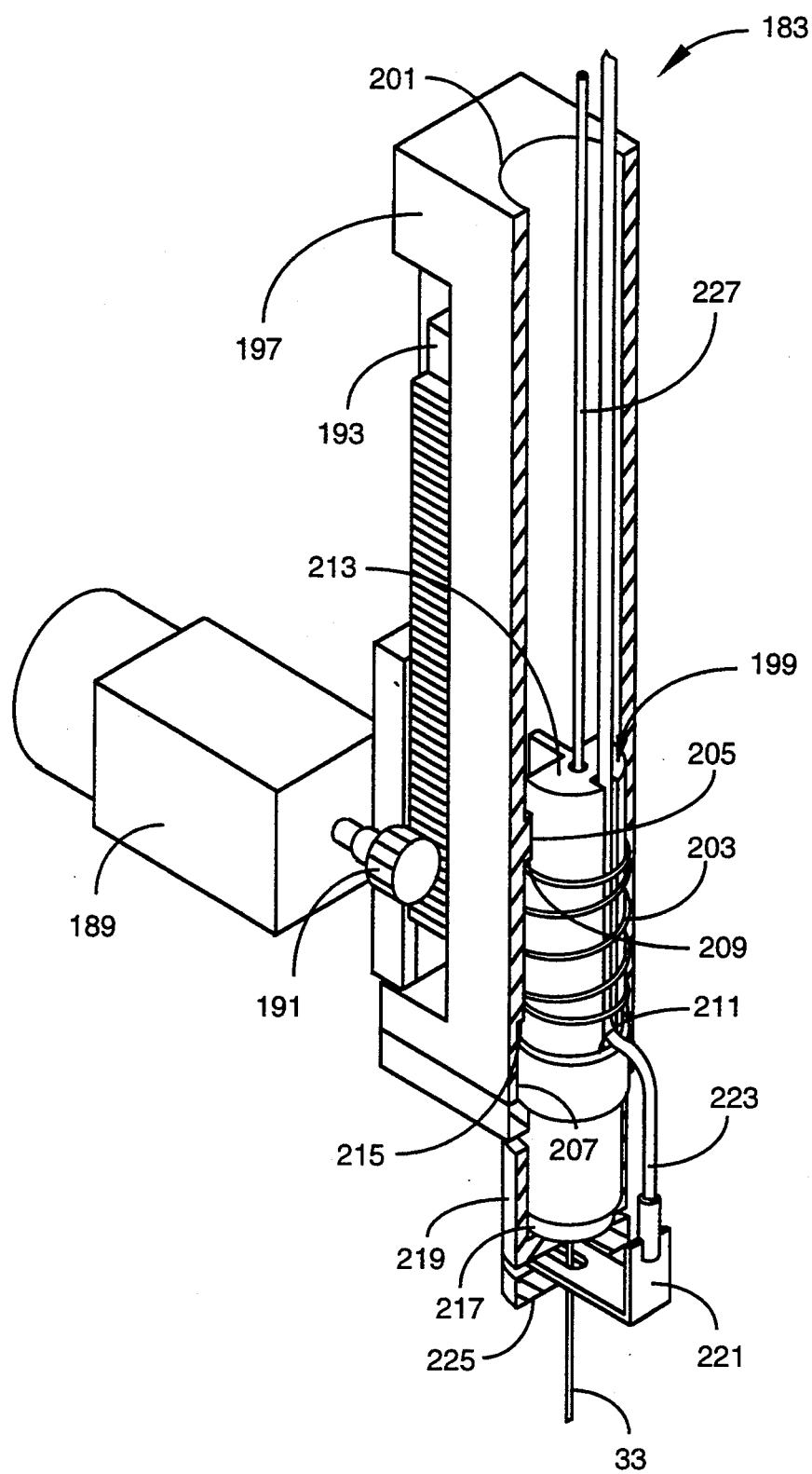
FIG. 3C is a perspective view, partially in section of a robotic assembly for vertical movement.

Although not shown in FIG. 3B, there are optical sensors in the preferred embodiment to signal positions of the Y-direction mechanism to the control system. A Z-direction mechanism 183 is mounted to a guide bar 185 and constrained to guide in a linear bearing 187 mounted to carriage 177 to provide motion in the vertical, or Z-direction. The Z-direction mechanism is driven by a D.C. motor 189 mounted to carriage 177 and turning a pinion 191 which in turn drives a rack 193 that is fastened to the Z-direction mechanism. The Z-direction mechanism protrudes through a slot 195 in plate 161. FIG. 3C shows additional detail of the Z-direction mechanism.

Block 197 of Z-drive mechanism 183 serves as a frame for other components. Rack 193 and the guide bar for the vertical guide linear bearing mechanism are attached to block 197. A probe assembly 199 with an outer body 213 is slidably engaged in a multi-diameter cylindrical bore 201 of the body with clearance for a coil spring 203. The bore diameter is smaller at regions 205 and 207, such that the clearance between the outside of body 213 and the guide diameters of the bore is about 0.1 mm., while the clearance in the region for the coil spring is about 1 mm. Spring 203 is captured between a shoulder 209 in block 213 and a shoulder 211 on body 213.

Body 213 is limited in vertical travel by shoulder 215 in block 197 and shoulder 211 on body 213. The vertical travel against the spring is for sensing contact with a resisting surface without damaging probe tip 33. Although not shown in FIG. 3C, there is a flag and optical sensor associated with the mechanism that signals when body 213 is lifted against spring 203.

Block 197 and body 213 in the preferred embodiment are made of an engineering plastic material to be non-conductive, such as nylon. There are several suitable materials. Tip 33 is stainless steel and brazed in the preferred embodiment to a stainless steel cylinder 217 which fits in a bore in body 213. A stainless steel thumb nut 219 threads onto body 213 and captures cylinder 217. A probe contact 221 connected to wire 223 supplies electrical potential to the probe tip, and is captured between thumb nut 219 and a thumb screw 225. Non-conductive polymer tubing 227 leads from the probe tip to the syringe pumps.

Figure 3D:
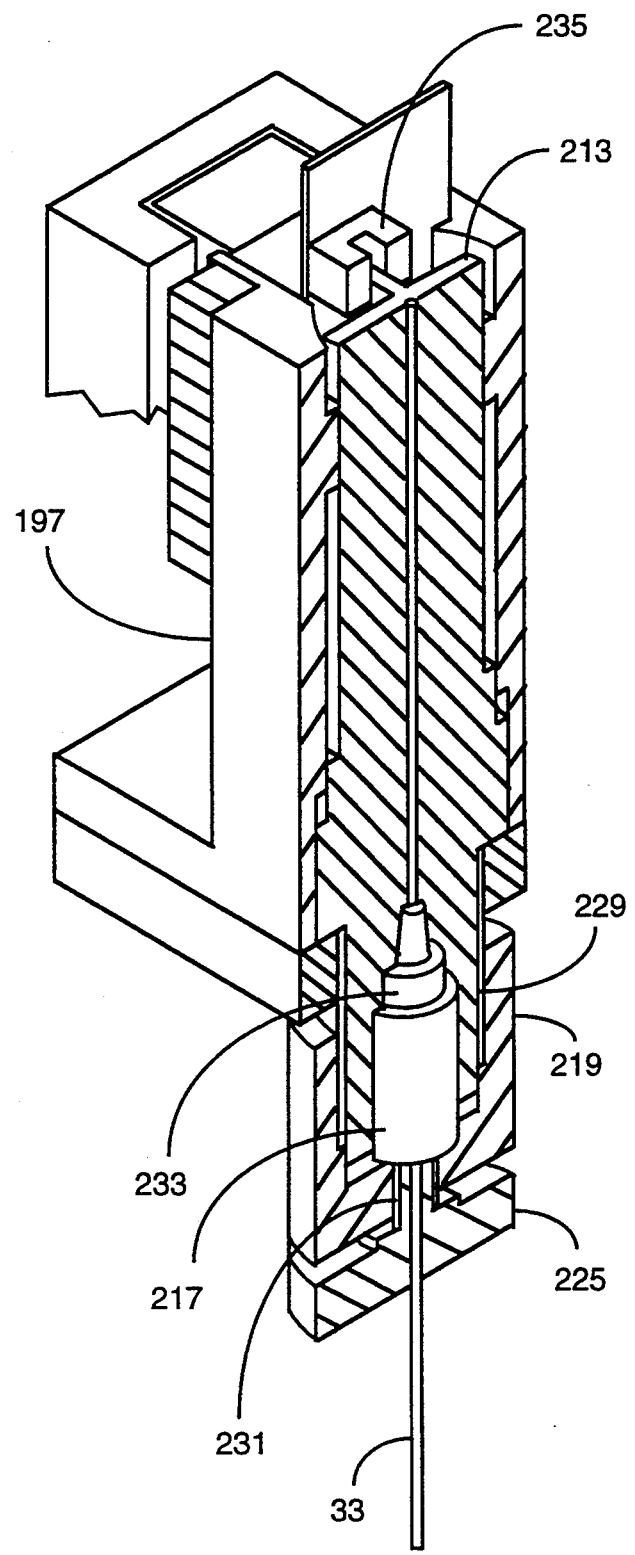
FIG. 3D is a perspective view in section of the vertical movement assembly showing additional detail.
Figure 3E:
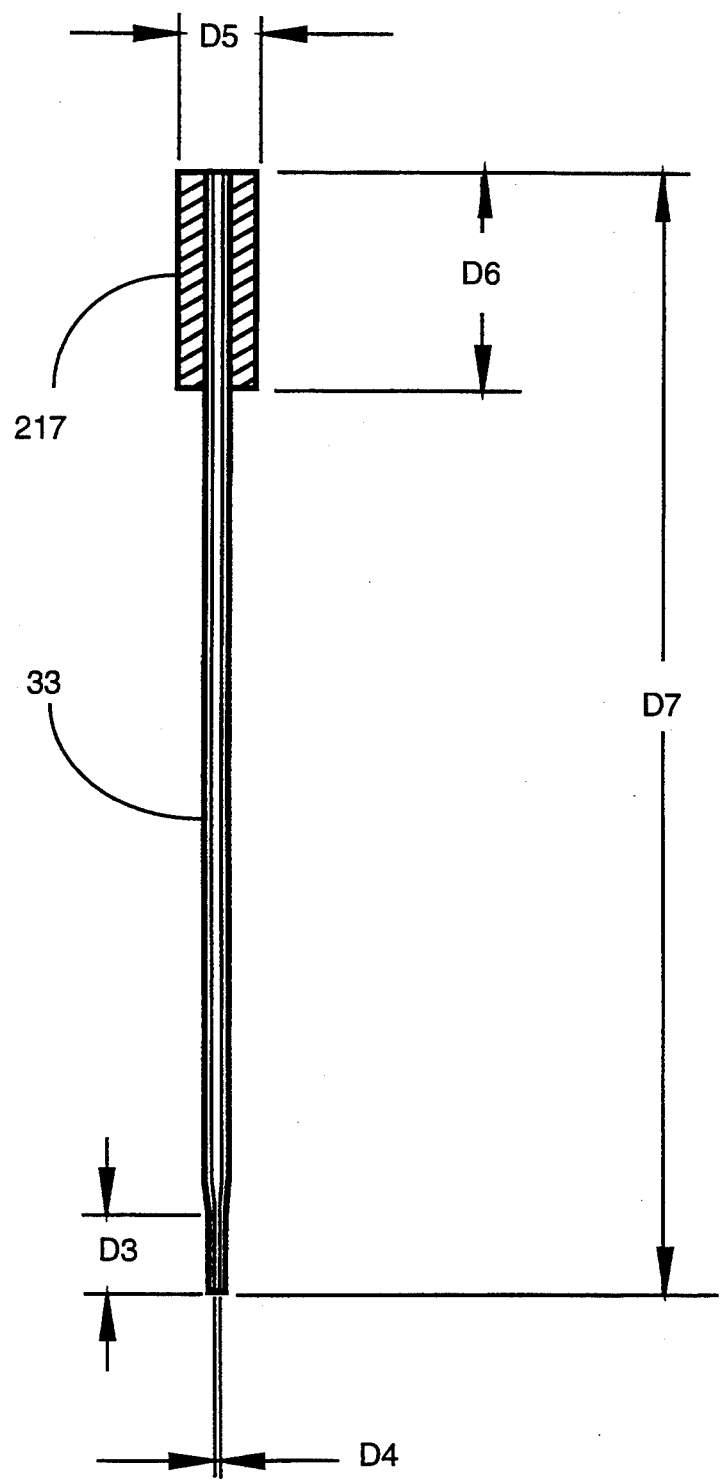
FIG. 3E is a view of a conductive pipette tip in the preferred embodiment.

FIG. 3D is a vertical section view of the probe assembly shown without the coil spring, contact 221 and the electrical wire. Body 213 in vertical section is shown engaged in block 197 with stainless steel cylinder 217 captured in a bore in body 213 by thumb nut 219 which engages body 213 by threads 229. Thumb screw 225 is shown threaded into thumb nut 219 by threads 231. The contact, which is captured between the thumb nut and thumb screw is not shown. Cylindrical element 233 is a separate piece for establishing a seal between the probe tip assembly and the delivery tubing by virtue of pressure applied with the thumb nut. Although the coil spring is not shown in FIG. 3D, an optical sensor 235 is shown that senses movement of body 213 in block 197.

Further detail of the probe tip is shown in drawing 3E. Probe tip 33 is part of a brazed assembly including stainless steel cylinder 217. Overall length D7 in the preferred embodiment is about 87 mm and the length D6 of cylinder 217 is about 20 mm. The diameter D5 of cylinder 217 is about 6.4 mm (0.25 inches). The tube portion is made of type 304 stainless steel tubing of about 1.27 mm (0.050 inch) outside diameter and about 0.8 mm (0.032 inch) inside diameter. For a length D3 at the tip end of about 6.4 mm (0.25 inches) the tube is narrowed so the inside diameter D4 is about 0.3 mm (0.012 inches). Having the diameter at the small dimension for only the tip end length is an advantage in that the flow resistance of the entire tube length is unaffected.

In the preferred embodiment the resolution in the X-direction is about 0.020 mm, in the Y-direction about 0.025 mm, and in the Z-direction about 0.015 mm. The control system in the preferred embodiment also provides speed ramping that can be varied by an operator through the unique operator interface, and capability to program special motions, such as a helical motion in the Z-direction to facilitate mixing operations. Such special motions are implemented as combinations of two or more of the basic X, Y, and Z motions.

The cartesian robot has a home position in the back, left corner of the work area (facing the AL), with the vertical drive at the full up position. This home position is determined by optical sensors built into each of the three direction mechanisms. For more accuracy than is possible with the optical sensor, a home position protocol is programmed in which the tip is moved slowly to touch each of three reference surfaces on a gauge block (block 24 in FIG. 1), and the robot position is recorded for each of the three points at the time that that capacitance sensing tip touches each of the three reference surfaces. This protocol is performed typically each time a new chemistry protocol is commenced.

Magnetic Separation

In chemistry protocols of the sort for which the present invention is intended there is often a need to separate material of one sort from other materials in a liquid sample. An example is in the purification of DNA samples to be sequenced. One way to accomplish separation in many instances is by use of paramagnetic particles coated with a substance with an affinity for the product of interest of the chemistry protocol. For example, such separation can be particularly useful in the context of ligand receptor binding, such as with biotin-avidin complexes.

In the AL, to accomplish this kind of separation, solutions to be separated are transferred to vials at one of the magnetic wash stations 26 or 29 (FIG. 1). The use of one or the other depends on whether heating or cooling during separation and washing is known to facilitate the process. Precoated particles suspended in a buffer solution are aspirated from a position at one of the reagent storage stations and dispensed into the solutions to be processed at the magnetic wash station.

FIG. 4A is a plan view of wash station 26, with heating and cooling capability. There are two rows of twelve tube positions each at the station. In the space between the rows of tubes there is a magnetic bar 237. FIG. 4B shows a section through the station of FIG. 4A taken along section line 4B—4B. Magnetic bar 237 is attached by connector 239 through a screw mechanism (not shown) to a D.C. motor 241. The motor is driven by the control system to move the magnet vertically between the rows of tubes, in the direction of arrow 243.

In the preferred embodiment the magnets used are composed of rare earth materials, for example, an alloy of Niobium and Boron with iron, to obtain a high strength magnetic field. The field strength in the area of the inside of the tubes is about 35 million gauss-oersteds.

In a typical sequence for separation and washing the magnets are raised after the paramagnetic particle suspension is added, and the particles are attracted into closely packed regions that are eventually located near the bottom of the tubes as shown by regions 245 and 247. The ability to move the magnetic bar for the full height of solution in the tubes and to stop it at various points allows the entire solution volume to be swept by the intense field and the particles to be collected into a small area efficiently. It is also advantageous to use a long tube with a small diameter as opposed to a shorter tube with a larger diameter, because the paramagnetic particles have a shorter distance to travel through liquid to be collected. By slowly lowering the magnetic bar the collected particles are moved to the bottom of the tube.

After moving the particles to the bottom, typically the remaining solution is drawn off and transferred to a waste container or discarded at the wash station to waste. It is not possible, however, to aspirate all of the liquid in the tube, leaving only the particles and the adhered product. To avoid contamination three wash cycles are typically accomplished.

Figure 4C:
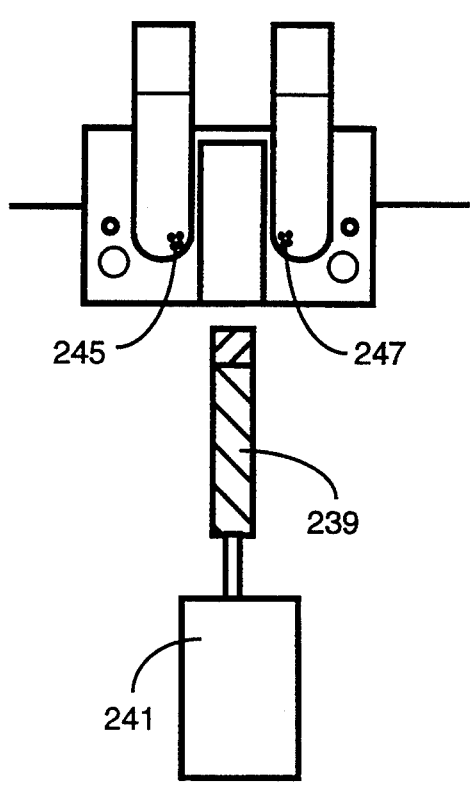
FIG. 4C is a section view similar to FIG. 4B, but with the magnet retracted.

For a wash cycle the magnetic bar is withdrawn to a lower position where the field from the bar will not effect the particles in suspension, as shown in FIG. 4C. The cycle starts with the particles at the bottom of a tube as shown by position 251 in FIG. 4D. Then wash buffer is aspirated at station 30 and dispensed into each of the tubes at the magnetic wash station where separation is being done.

Figure 4D:
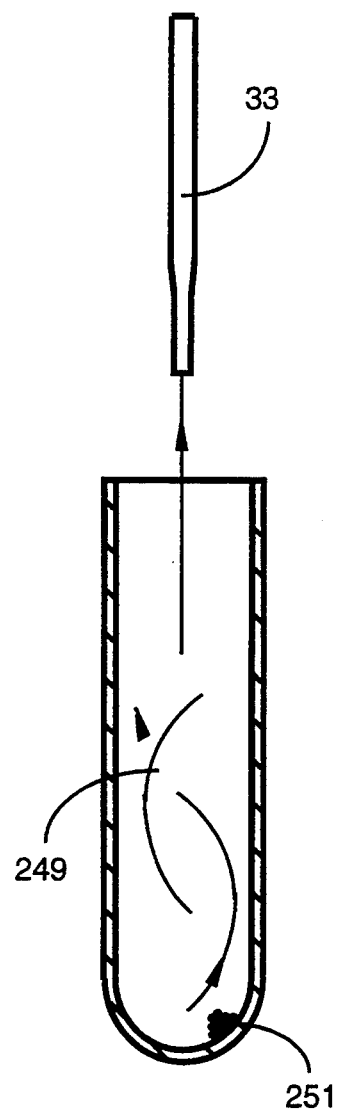
FIG. 4D is a section view of a tube of liquid showing a pipette tip and a helical path used for mixing liquid.

Typically, to help re-suspend the particles, the wash buffer is added with a programmed helical motion from near the bottom of a tube until all of the buffer is added, imparting a stirring action as the buffer is added. FIG. 4D shows a vertical section of one of the tubes of FIG. 4C and the pipette tip of the AL. The helical motion of the tip while dispensing wash buffer is approximated by path 249, and is pre-programmed using motions in all three directions X, Y, and Z. After adding the buffer, if another wash cycle is programmed, the magnetic bar is raised again to re-collect the particles. The action can be repeated as often as necessary, and is typically done four or five times.

Robotic Interface

A unique program is run on the computer in the preferred embodiment to create control programs, enter and edit variable values, and to initiate and terminate process sequences. The program, hereinafter called Popframes, is an iconic program that employs graphic symbols called icons to represent processes, process steps, and other activities, and is described in copending patent application entitled ROBOTIC INTERFACE, Ser. No. 07/423,785 referenced earlier. Popframes provides a unique user interface that is useful for handling hierarchical information and for controlling many kinds of process machines and equipment.

Popframes has a set of routines allowing a user to select icons representing various activities and to organize the icons into flow schematics representing process flow, with the icons connected on the display with lines. The icons may also be nested such that a relatively complex sequence of activities may be represented by a single icon, and the single icon may be expanded in place to show a connected sequence of icons representing steps in the more complex sequence. The second level icons may also consist of sequences of other icons, also expandable in place, until, at the lowest level, icons represent fundamental process steps. The fundamental steps in the preferred embodiment are typically themselves sequences of even more basic activities. For example, a fundamental step may be a direction by the program to the AL to send the robot arm to a specific position at the DNA stage, station 28 in FIG. 1. The command from the computer to the electronics interface is equivalent to "Go to position X at station 28." The position is a known site to the control system, and sensors tell the control system where the robot arm is before the move. Quick calculation determines the magnitude of the X, Y and Z moves to reach the destination from the starting point. The system then accomplishes the necessary drive sequence with default acceleration and velocity.

Figure 5A:
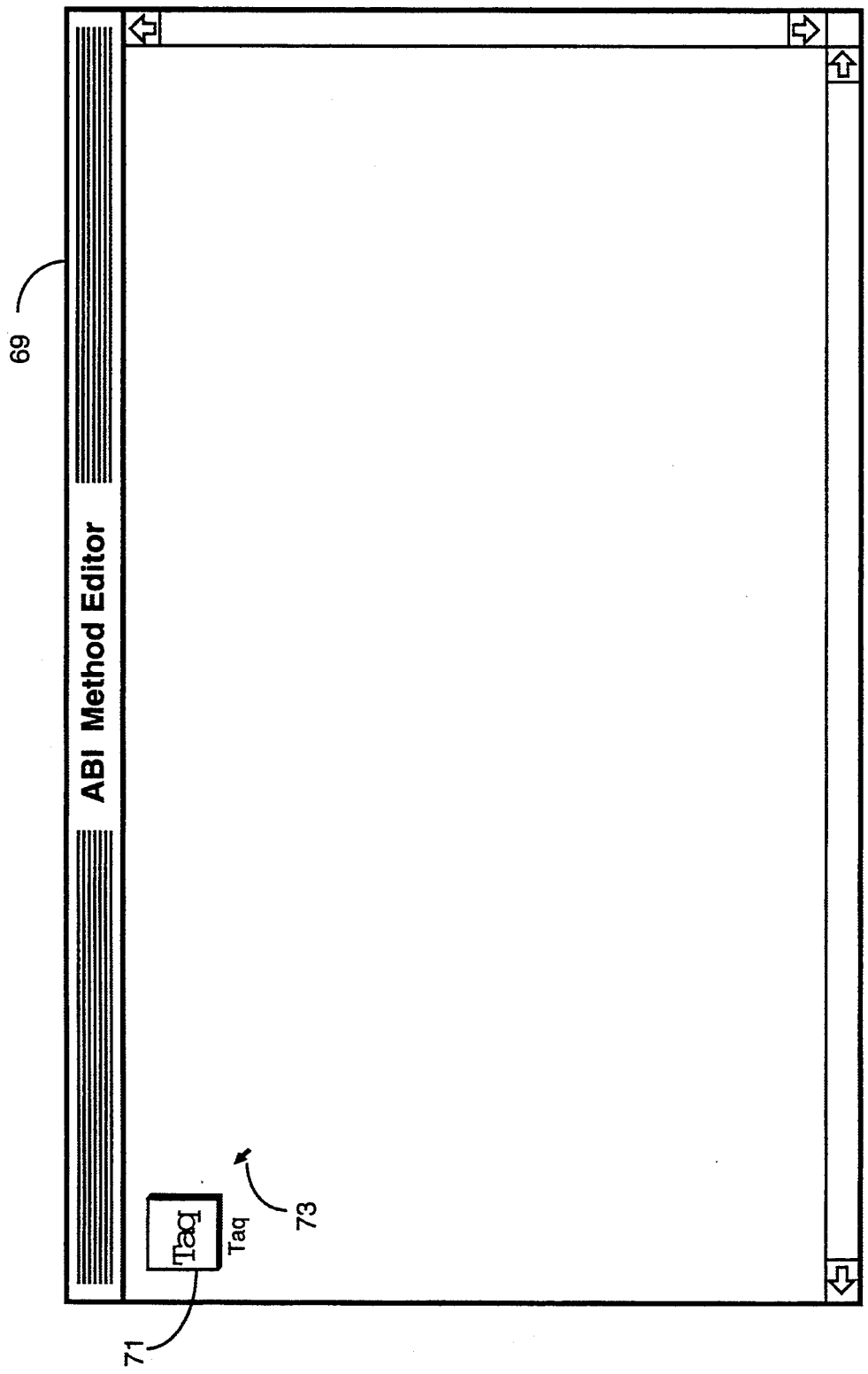
FIG. 5A is a view of a computer display showing a high-level icon representing an automated chemistry protocol.

FIG. 5A shows a screen display 69 in Popframes with a program icon 71 for the Taq DNA sequencing protocol. The single icon represents all of the steps and procedures of the protocol of sequencing DNA templates by the Taq procedure described above. A screen cursor 73 is movable over the area of the screen by moving mouse device 19 over a surface. This is a phenomenon very familiar to those skilled in computer arts.

By placing the cursor at the top-level Taq icon and pressing a button on the mouse twice, a procedure known in the art as "double clicking", a user can expand the Taq icon to see other icons representing more detail of the Taq DNA sequencing procedure.

Figure 5B:
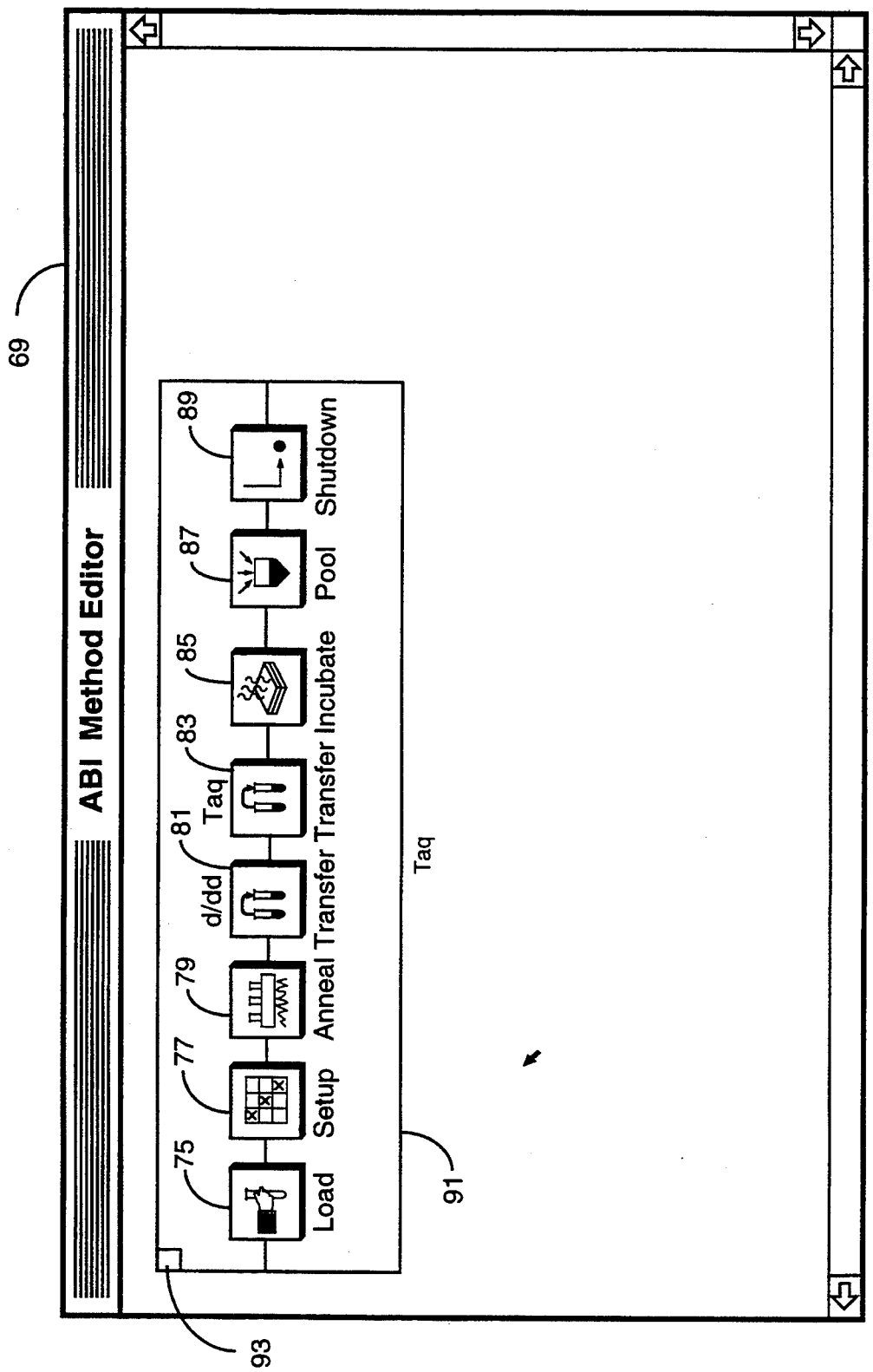
FIG. 5B is an expansion-in-place of the icon of FIG. 5A.

FIG. 5B shows the result of expanding the Taq icon in place. There are then eight icons shown in an orderly sequence representing eight sequential parts of the overall procedure. The eight are: Load 75, Setup 77, Anneal 79, Transfer d/dd 81, Transfer Taq 83, Incubate 85, Pool 87, and Shutdown 89. The Taq program icon is represented in the expansion by a box 91 surrounding the eight icons shown in sequence. There is a hierarchical relationship between the original icon, which is at the top of the hierarchy, and the sequence of eight icons of FIG. 5B, which are at one level below the top level icon. The labeling of the surround box: Taq, preserves the relationship so information is not lost.

A user can reverse the expansion process, collapsing a sequence of icons into a higher level icon. The method is by clicking on the close box 93 at the upper left corner of the Taq box within which the eight icons appear. Clicking means that the cursor is moved to the close box, and the mouse button is pressed once. The expansion then collapses back to the original Taq icon at the highest level. The highest level icon does not have a close box, because none is needed, but boxes at all levels below the highest level do have close boxes.

Figure 5C:
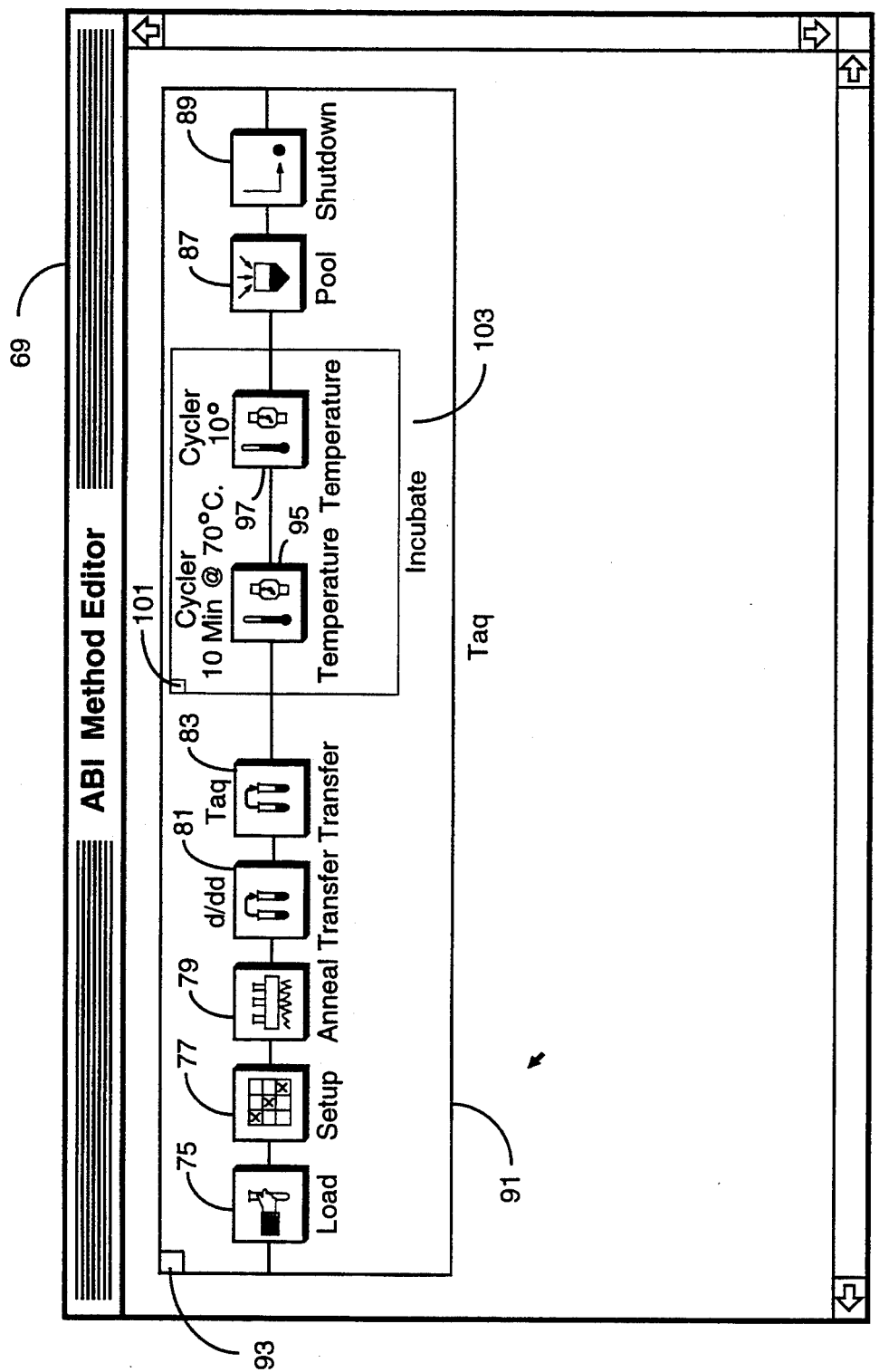
FIG. 5C is an expansion-in-place of one of the icons of FIG. 5B.

FIG. 5C shows the expansion result initiated by double clicking on the Incubate icon in FIG. 5B. After expansion, the Incubate process is seen to be composed of two distinct steps, step 95 to cycle 10 minutes at 70 degrees C., and step 97, which cycles the temperature after 10 minutes at 70 degrees C. to 10 degrees C. In FIG. 5C the Incubate icon has become the surround box 103 with a close box 101. The hierarchical relationship of the entire program is still preserved.

Figure 5D:
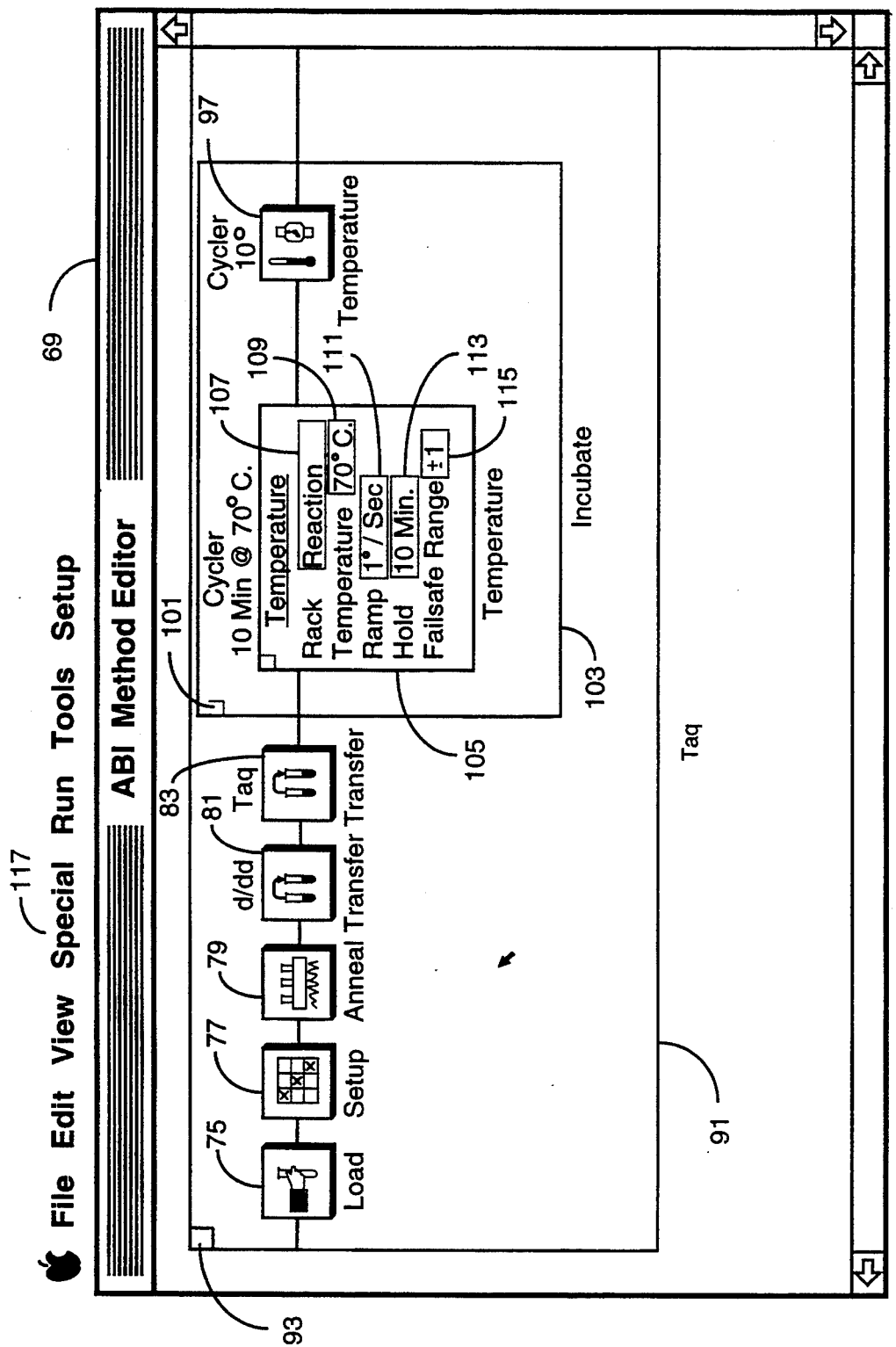
FIG. 5D is a further expansion-in-place of an icon of FIG. 5C.

The expansion of step 95 by double clicking illustrates yet another feature of the iconic program in the preferred embodiment. FIG. 5D shows the expansion of step 95 as a variable-entry box 105. Box 105 is at the lowest level of the hierarchical relationships in the iconic scheme, and provides several text fields for entering information for the computer to follow when performing the step. Rack entry field 107 allows a user to enter the name of the rack where the temperature cycling is to be done.

A user makes an entry by clicking on the text field, which enables the field for entry, then entering the designation of the rack from the keyboard. The entry field, while entry is being made, works much like a word processor. If a mistake is made, the backspace key allows the user to correct the error.

Temperature field 109 is for setting the temperature for the temperature step. Ramp field 111 is for setting a ramp rate for changing the temperature. Hold field 113 is for entering a time for holding the temperature at the set temperature. Failsafe field 115 is for entering a temperature range for deviation from the set variables without aborting the process.

At the point in expansion illustrated in FIG. 5D, the expansion has become too broad to be shown on the screen, and the Taq surround box shows terminated at the right edge of the screen. By placing the cursor inside the Taq surround box, holding down the mouse button and moving the mouse, a user can move the display to show the hidden portion at the right. This is a process called panning in the art. By panning a user can still see all of an expanded program, so information about the hierarchical relationships of the program is always preserved.

The description above for the Taq sequencing protocol shows only a few of the expansions possible for that particular program. At the lowest level of expansion of each of the other icons there is a variable-entry box. For example, at the lowest expansion level of the setup box, there is a variable-entry box with fields for the user to relate specific sites at each station to specific samples and reagents that are to be loaded for the analytical sequence.

In addition to the ability by text entry fields to vary many process parameters within a particular protocol, like the Taq sequencing protocol, there is also an ability to alter the steps and the sequence of steps, and to create entirely new and different programs. Functions for program creation and alteration are listed under menu headings in a menu bar, normally hidden from the user. With an appropriate key combination the menu can be displayed.

There are, in the preferred embodiment, eight drop-down menus in the menu bar, labeled Setup, Tools, Run, Special, View, Edit, File and another headed by an Apple icon. The functions of these menus are further described in the co-pending ROBOTIC INTERFACE specification.

Procedure Example

Figure 6A:
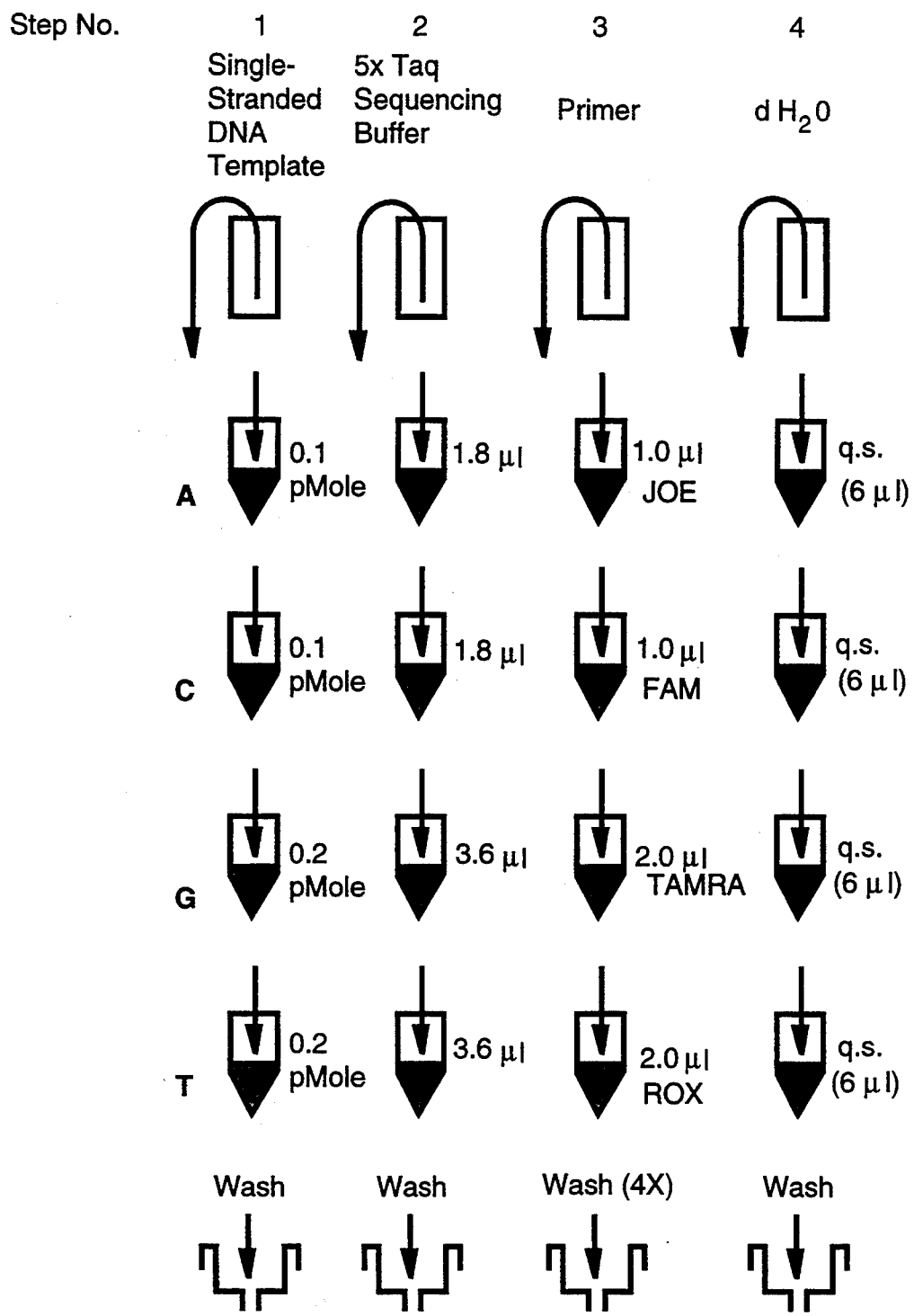
FIG. 6A is a schematic representation of some steps of an example chemistry protocol for the preferred embodiment.
Figure 6B:
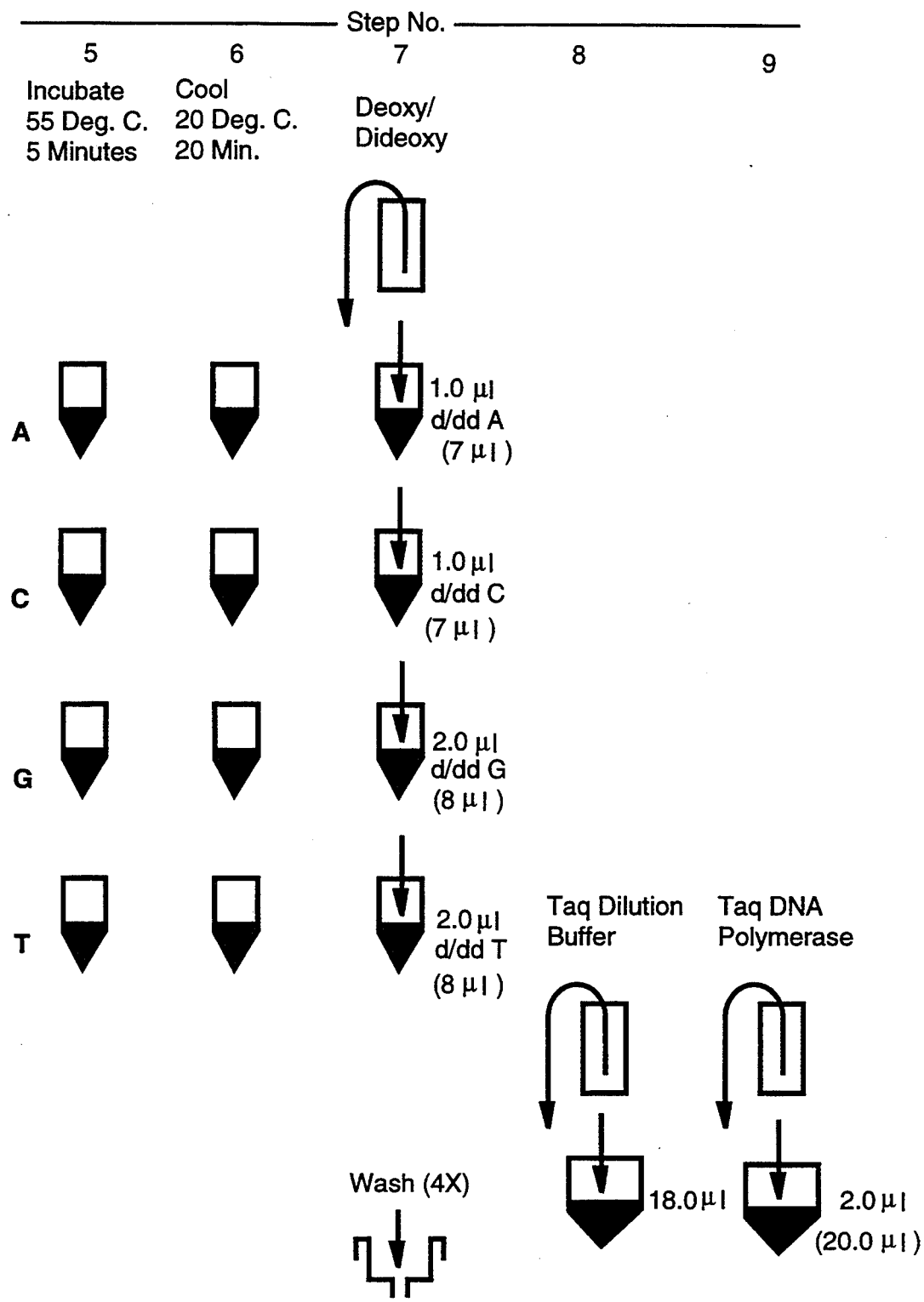
FIG. 6B is a representation of further steps of the example protocol of FIG. 6A.
Figure 6C:
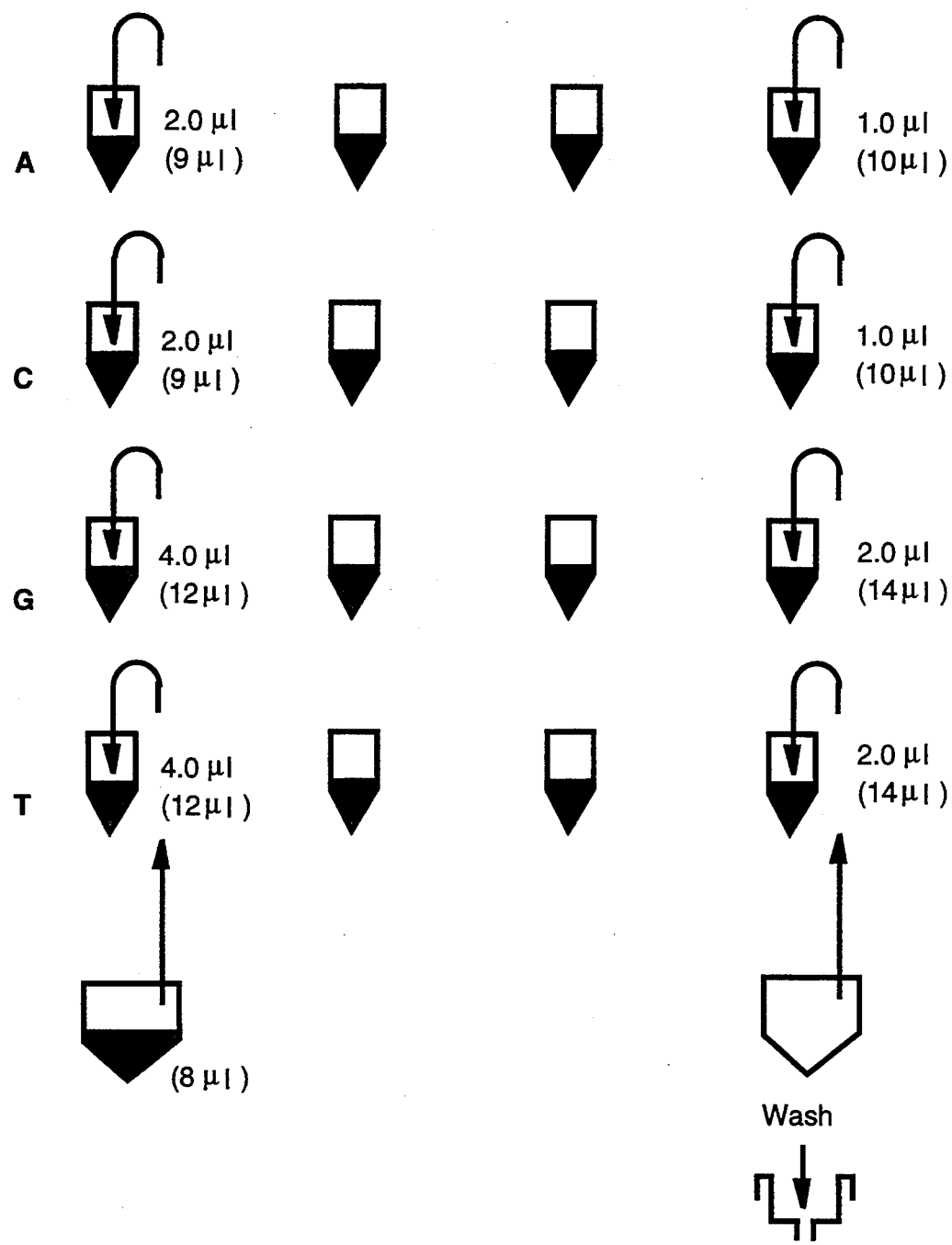
FIG. 6C is a representation of further steps of the example protocol of FIG. 6A.
Figure 6D:
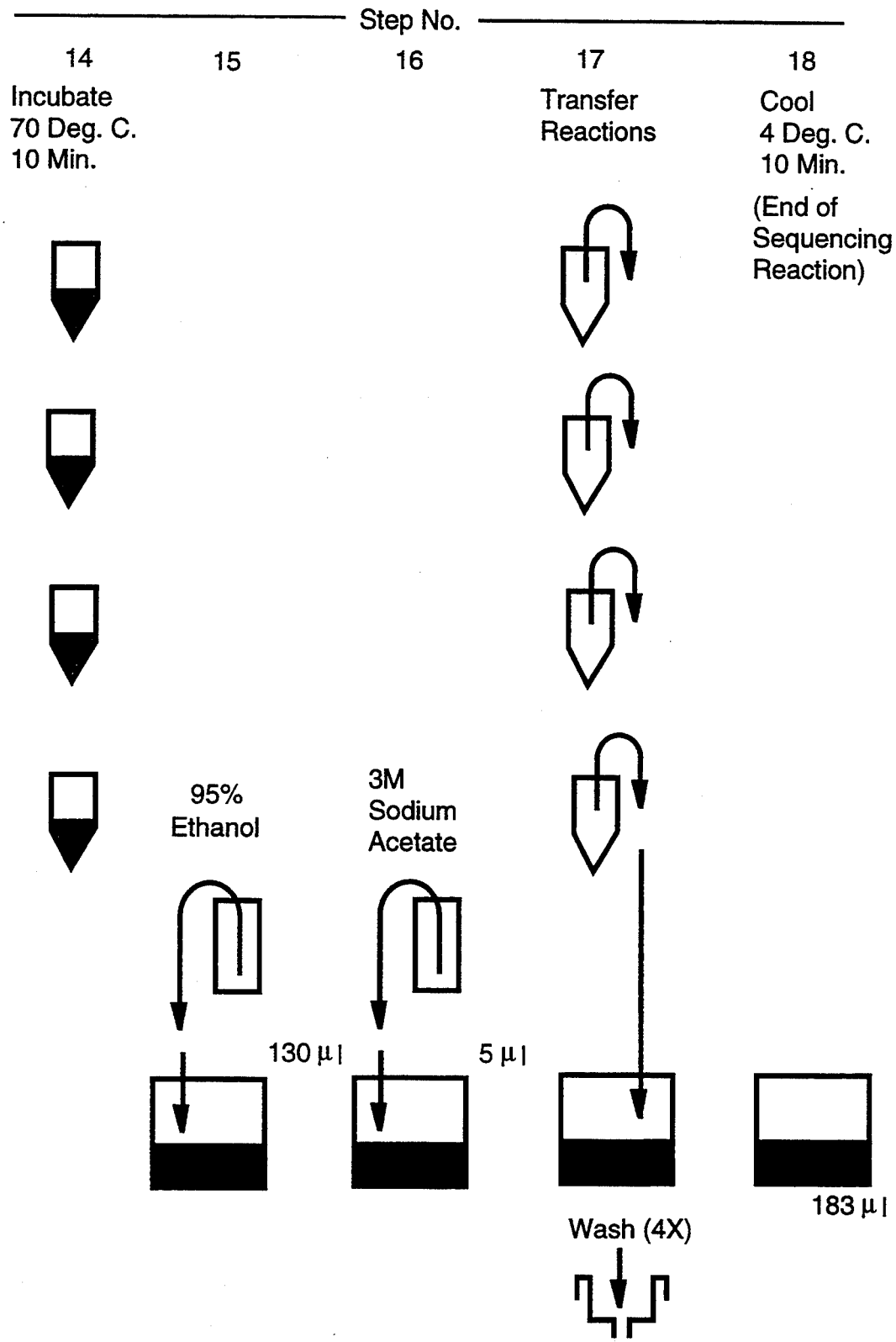
FIG. 6D is a representation of still further steps of the example protocol of FIG. 6A.

FIGS. 6A, B, C and D illustrate a typical biochemical procedure performed on the AL in the preferred embodiment, and is illustrated both as an example of use and as a basis for further description of apparatus and methods in preferred embodiments of the invention. The example illustrated is a proprietary Applied Biosystems, Inc., protocol based on the Sanger termination method for DNA sequencing with Taq polymerase, performed on one single-stranded DNA template.

Each column in FIG. 6A, 6B, 6C and 6D represents one step in an automated protocol, with the progression of steps numbered at the top of the columns, reading from the left to the right through the four Figures. The liquid volume dispensed to a container in any operation is listed to the right of the container, and the total liquid volume in the container is in parentheses. The protocol involves only three mechanical functions in the automated system: robotic positioning of the pipette tip, small-volume liquid handling through and with the pipette tip, and heating and cooling.

The user begins the chemistry by loading tubes of the DNA template to be sequenced and the necessary reagents in the robotic system. The DNA sample tubes are loaded to station 28 (FIG. 1), the DNA stage in the preferred embodiment. In the particular protocol illustrated there is a requirement for four samples of the same DNA template. Typically, several different DNA templates would be sequenced, and the 96 position array at the DNA stage in the preferred embodiment allows 24 different templates to be sequenced at the same time.

In the Popframes software system used to control the AL in the preferred embodiment there is facility to relate specific sites at specific stations with DNA templates and reagents, so the system "knows" where to find templates and reagents, and there is facility also, for programming sequences such as the Taq gene scanning sequence described, so the system "knows" what steps to perform in what order. It is assumed in this example that the programming has been done for Taq sequencing.

In steps 1 through 6 dye-labeled primers are annealed to the DNA template. In step 1 DNA template is moved from the DNA stage to containers at the thermal cycling station 23 (FIG. 1). One template is prepared for each of the four base types A, C, G and T. Taq sequencing buffer is moved in step 2 from reagent storage station 27 to the containers at the thermal cycling station in the amounts shown in the Figure. In step 3 the dye-labeled primers are added, and in step 4 pure water is added to each reaction container.

At step 5 the lid is closed at station 21, heat is applied, and the dye-labeled primers are annealed to the DNA templates at 55 degrees C. for 5 minutes. In step 6 the reaction containers are cooled at 20 degrees C. for 20 minutes. In steps 7–14 the Taq DNA polymerase synthesizes complimentary DNA chains along the DNA templates to the dideoxynucleotide terminations. The Taq enzyme is deactivated in the alcohol precipitation of steps 15–18. At step 18 the product is ready for flourescent sequencing by gel electrophoresis.

In the process described here for 24 templates processed in parallel, the robot makes 751 moves, or 31 moves per template. For laboratories that process up to hundreds of samples per week, the number of necessary moves provides motivation for automating the protocol. In this particular protocol the magnetic wash stations are not needed, but they are useful in other protocols, such as gene scanning.

Another example of a specific molecular biology processes that the apparatus has been used to perform is provided in the section of this specification titled "Appendix A—A Further Application Example". The examples presented are not intended to limit the application of the apparatus, which is useful for many other procedures in chemistry. Applications comprise automated specific gene detection, automated nucleic acid sequence detection, and automated fluorescent labelling of nucleic acids, among other procedures.

Liquid Handling

All of the robotics in the AL are involved with handling of small volumes of liquid to accomplish chemistry protocols. Some of the liquids are quite vicous, such as genomic DNA. Others are much less viscous, such as water. A significant difference from previous equipment is in the fact that the AL of the invention uses a single pipette tip rather than throw-away pipettes as is typical in previous machines. Also in the preferred embodiment unique equipment and methods are employed to reduce evaporation to a minimum and to facilitate handling of samples and reagents to and from the AL.

FIG. 7A is a perspective view of a tube closure 253 used in the invention to prevent evaporation of materials during processing, and to provide other advantages. Closure 253 is called a duck-billed closure, and is shown assembled to a tube 255 of a sort often used for samples, enzymes and reagents. Closure 253 is molded from a flexible material, typically butyl rubber in the preferred embodiment. Such duck-billed closures are a feature useful in many, but not necessarily all, applications of the present invention. The closures are most useful in embodiments where problems related to evaporation are potentially more serious than in other applications.

FIG. 7B is a vertical section of the tube and closure shown in FIG. 7A along the section line 7B—7B. FIG. 7C is a vertical section of the same assembly along the section line 7C—7C, taken at a right angle to section 7B—7B.

The duck-billed closure in the preferred embodiment has a seal portion 252 with a cavity, usually circular, for enclosing the upper rim of a container to be closed. There is a flexible duck-billed portion 254 extending into the container from above, such that a needle-like device, such as the probe tip in the preferred embodiment, may be easily inserted from above and withdrawn to access liquid in the container. When the probe tip is inserted, the duck-billed closure remains urged against the tip with a bare minimum of opening for possible escape of liquid or vapor. When the tip is withdrawn, the duck-billed closure closes, and effectively prevents liquid or vapor escape.

The outside diameter D8 of the closure in the illustrated embodiment is about 13.2 mm. Dimension D9, the width of the duckbill portion is about 4.8 mm. The height D10 of the duckbill closure is about 7.1 mm. The included angle A1 of the duckbill portion is about 45 degrees. The wall thickness D11 of the duckbill portion is about 0.25 mm. These dimensions are for a closure for a particular tube, and will vary depending on the tube to be closed. Other embodiments will have different dimensions.

Figure 8:
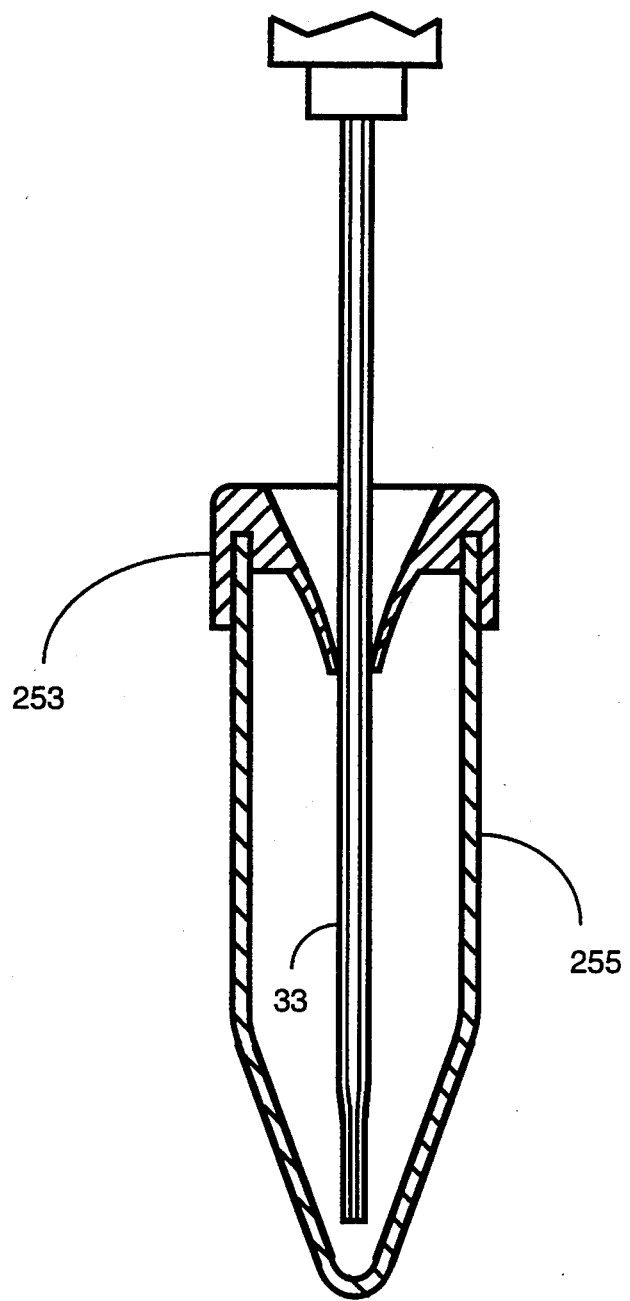
FIG. 8 is a section view through an assembly of a duck-billed closure and a container showing a pipette tip inserted through the closure.

FIG. 8 shows the tube and closure of FIG. 7A, B, and C with a probe tip 33 inserted. The tip can penetrate the closure from above with little effort and be withdrawn with little effort as well. In penetration or withdrawal there is no mechanism or motion involved more than is involved if there is no closure at all, and the duckbill is caused to open only the exact amount needed to admit the probe. In other closure schemes, such as a snap-on lid, additional mechanism and robotic control must be provided to open and close the lid for access to the contents of a tube. The duckbill closure effectively prevents evaporation, eliminating inaccuracies and cross-contamination that evaporation can cause. At stations where heat is applied the duckbill closure not only prevents evaporation, but effectively seals against small buildup of pressure inside the tube.

There are other advantages to the duckbill closure. For example, reagents and other materials used in the AL can be packaged for transport with the duckbill closure in place, avoiding need to transfer the contents from one container to another during setup of the AL for a protocol. This is useful because it is very common to use a device like the AL at one site and to prepare samples and other materials at another. Moreover, most reagents are prepared by supply houses and sold to laboratories, who seldom prepare their own. The use of a duckbill closure in the original packaging can avoid potential for error and contamination. In the process of packaging with a duckbill closure, a secondary secure cap can be applied for shipment and removed at the use site without disturbing the contents.

Another advantage of the duckbill closure is that tubes can be removed from the AL after chemistry protocol and transferred directly to a centrifuge in those cases where centrifuging is desirable.

As was explained above, handling a very small volume of liquid very accurately with a pipette is a delicate and exacting procedure. It is no simple task manually, and the difficulty of duplicating the manual procedure sufficiently accurately has been an impediment to the development of useful robotics for automating laboratory procedures. The advances of the present invention, particularly in the area of robotic position resolution and repeatability and delicacy of maneuvering, combined with accurate capacitance surface sensing, have made it possible to develop programmed techniques to accomplish very accurate liquid transfers, both aspiration and dispensing. One such technique developed for the present invention is droplet conveyance, and has been called the "kiss off" technique. It is used to avoid problems associated with droplet formation and as a technique for transferring known volumes of liquid in discrete droplets from one container to another on the AL.

Figure 9D:
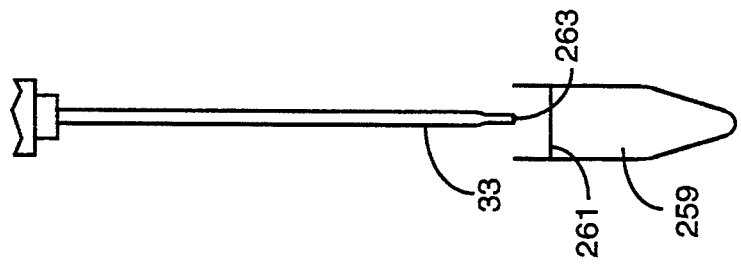
FIG. 9D shows still another step of the method of FIG. 9A.
Figure 9C:
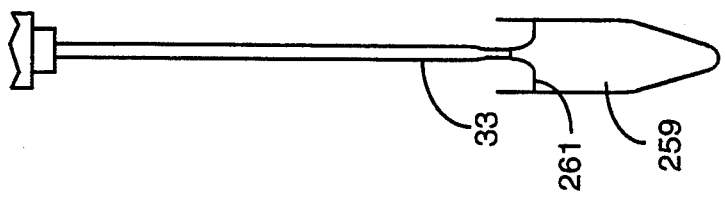
FIG. 9C shows yet another step of the method of FIG. 9A.
Figure 9B:
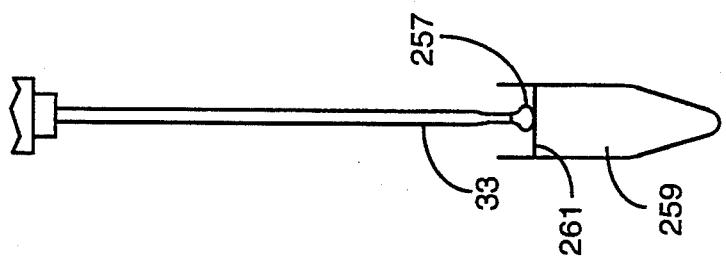
FIG. 9B shows another step of the method of FIG. 9A.
Figure 9A:
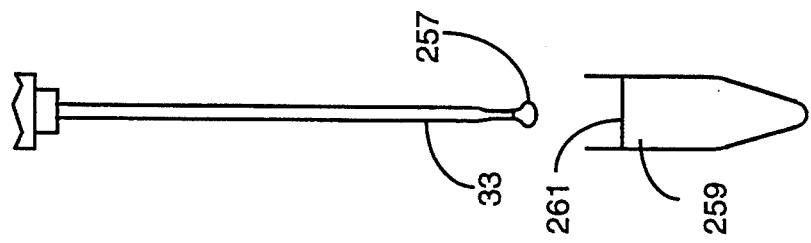
FIG. 9A shows one step of a method for transferring a droplet of liquid with apparatus according to the preferred embodiment.

FIG. 9A shows the pipette tip 33 in the preferred embodiment with a droplet 257 of liquid formed on the end. The tip and droplet are shown positioned over a vial 259 containing a liquid having a surface 261. A droplet is typically formed by aspirating liquid with the pipette, then driving a syringe pump to dispense just enough liquid to cause a droplet to form. The size of the droplet is determined by such factors as the diameters and material of the pipette tip, the angle, if any, on which the tip is cut, the material to be piperted, the volume driven by the syringe pump, the temperature, and other factors.

In the droplet conveyance technique the probe tip with a droplet on the tip is lowered to a liquid surface, and the probe tip is stopped just as the droplet touches the surface. The point at which the droplet touches the liquid surface is known by the capacitance sensing ability of the robot control. The robot waits while the droplet transfers to the liquid, a process known as confluence, then the tip is raised. FIG. 9B shows the pipette of FIG. 9A lowered toward vial 259 to the point that droplet 257 just touches liquid surface 261 in the vial.

FIG. 9C shows the situation a fraction of a second after the droplet touches the liquid surface. The droplet is merging with the liquid in the vial and is still adherent to the tip by virtue of the surface tension of the liquid. FIG. 9D shows the situation after raising the tip. The liquid surface has separated from the liquid still in the pipette tip and from the pipette tip, leaving only a small miniscus 263 at the end of the tip. The droplet conveyance technique is used in the preferred embodiment to transfer discrete volumes of liquid as small as 1 microliter.

The kiss-off technique is a series of movements for the AL that are programmed into a reusable sequence with an icon, and can be placed in new sequences as required using the Popframes programming interface described above.

Another liquid handling technique that has been developed in the preferred embodiment is a technique of accurately aspirating liquids with the pipette tip while minimizing contamination of the tip. The technique is particularly applicable to handling viscous liquids, which are generally more troublesome in liquid handling than are less viscous liquids. FIGS. 10 A, B, C, and D show the steps used in this technique.

Figure 10D:
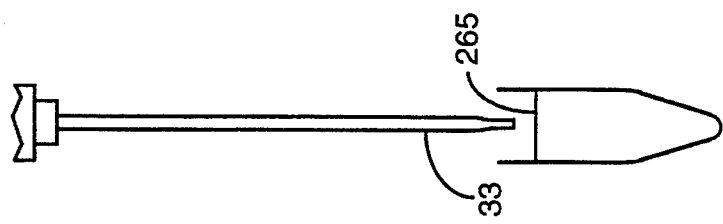
FIG. 10D shows still another step of the method of FIG. 10A.
Figure 10C:
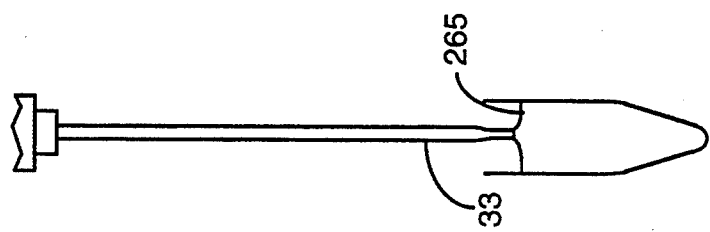
FIG. 10C shows yet another step of the method of FIG. 10A.
Figure 10B:
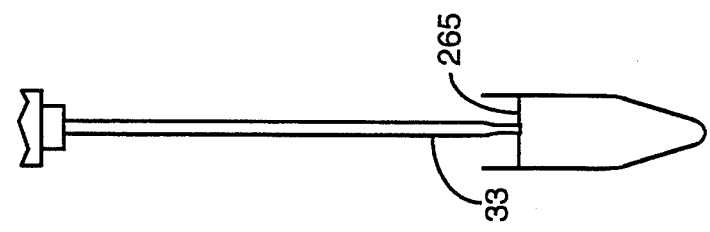
FIG. 10B shows another step of the method of FIG. 10A.
Figure 10A:
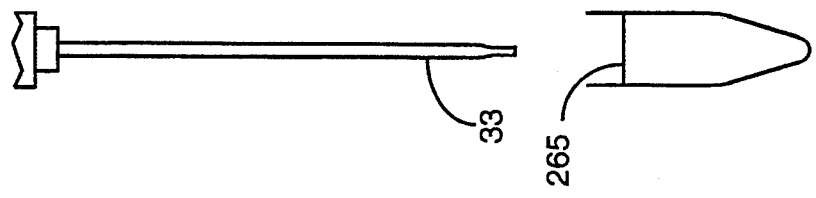
FIG. 10A shows one step of a method for aspirating liquid using apparatus according to a preferred embodiment.

First, probe tip 33 is positioned over the surface 265 of a liquid to be aspirated, as shown in FIG. 10A. Next the tip is lowered to touch the surface, sensed by the capacitance sensing ability associated with the probe tip, as shown in FIG. 10B. Aspiration of a programmed amount is accomplished slowly, typically at about 1 micro-liter per second, while the tip is at the surface as shown in FIG. 10B. The rate of aspiration is set to suit the viscosity of the liquid to be aspirated. If the amount to be aspirated is quite small relative to the volume in the container then the tip position will not have to be adjusted vertically during the aspiration. If, however, the amount to be aspirated is large enough that the position of surface 265 might change enough to cause a problem, the position of the tip can be adjusted downward during the aspiration to maintain the relationship of the tip to the liquid surface. Alternatively, after the surface position is known by the capacitance sensor, the pipette tip can be lowered a fixed small amount to penetrate the liquid surface a minimal amount before aspiration begins.

After the liquid is aspirated, the probe tip is slowly withdrawn, typically at a rate of about 1.5 mm per second. As the tip is withdrawn, initially liquid still clings to the tip as shown in FIG. 10C, and this condition varies depending on the viscosity and surface tension of the liquid. The tip and the liquid separate as withdrawal continues, as shown in FIG. 10D. The probe is then moved to wherever is required to dispense the liquid that has been aspirated. The aspiration technique is a series of movements for the AL that are programmed into a reusable sequence with an icon, and can be placed in new sequences as required using the Popframes programming interface described above.

For liquids with low viscosity, such as water, it is frequently desirable to aspirate an air gap at the pipette tip after aspirating a volume of liquid, so movement of the pipette by the robot does not cause liquid to be dislodged from the pipette.

To avoid contamination, previous robotic devices have typically relied on discarding pipette tips after a single use, and in many cases on discarding vials and other containers as well. For example, in the incubation portion of the Taq DNA sequencing protocol used as an example in this specification, materials are moved to a closable-lid incubation station where the reaction vessels are machined into a coated aluminum plate. One of the reasons for having the reaction vessels machined into the plate is to provide a good heat transfer path to the liquid material to be heated in a reaction vessel. In prior devices the possibility of contamination is handled by throw-away liners or disposable reaction vessels, but disposable vessels lead to variability in heating and cooling.

The use of disposable pipette tips presents more than one difficulty. Capacitance sensing for calibration, surface sensing and other purposes is rendered difficult or impossible with disposable tips, particularly plastic tips, so accuracy cannot be attained and maintained. Further, there are many transfers to be made in a useful protocol, as described above, so as many as a thousand disposable tips would have to be stored, and the ability to dispose and replace the tips has to be programmed. Moreover, the process with disposable tips requires much more time, space, mechanism, and attendant possibility of error.

In the present invention advances in robotic equipment and technique, such as capacitance surface sensing and the Popframes programming and operating interface, make it more practical and easier to operate with a single pipette tip and to wash the tip between liquid transfers. Washing is adequate to avoid contamination, in part because of the liquid handling techniques described above, which limit exposure of the exterior of the tip to the liquids being handled.

Figure 11:
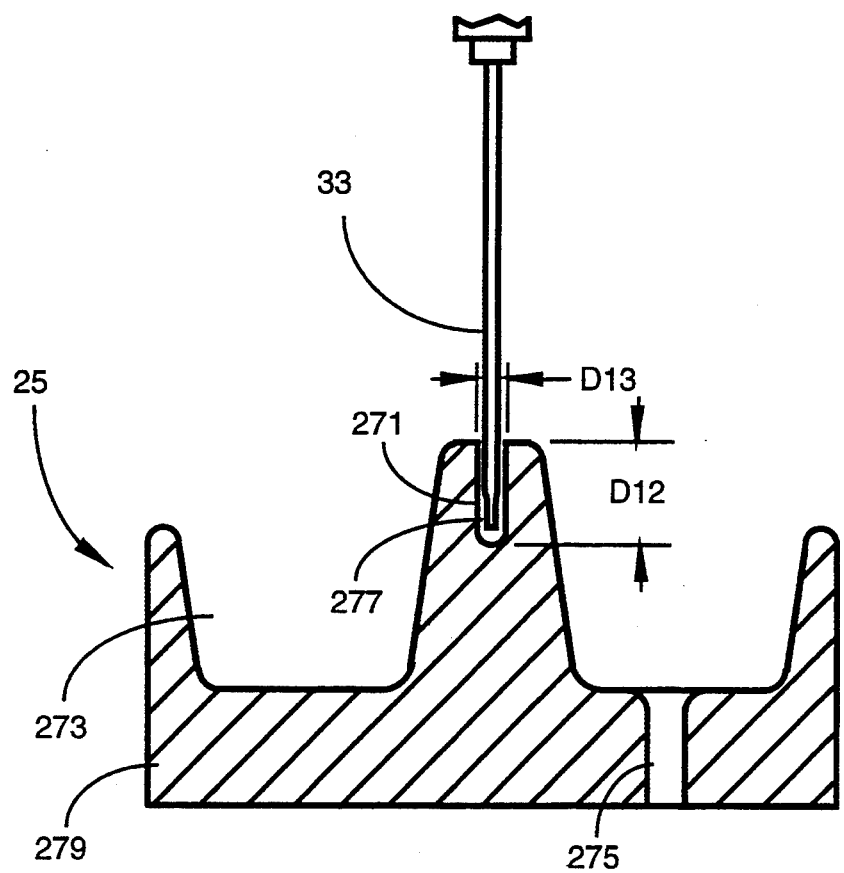
FIG. 11 shows a section through a wash station in a preferred embodiment.

In the preferred embodiment wash station 25 is used as needed between liquid transfers to cleanse the tip before a different reagent or sample material is transferred. The tip can be washed both inside and outside. FIG. 11 shows the pipette tip in position to wash the tip at wash station 25. The wash station includes a body 279 with a fountain 271, a well 273 and a drain 275. Body 279 is shown in section so the position and nature of other components may be seen. The fountain is a generally cylindrical bore of a depth and diameter such that wash buffer dispensed from the pipette tip will backflow and wash the outside of the tip. In the preferred embodiment the tip dimensions may vary for different protocols and purposes. In one case the tip is about 0.6 mm in outside diameter for a length from the end of about 6 mm. For this particular tip the depth of the fountain D12 is about 6 mm and the diameter D13 about 1.2 mm. The requirement is to provide an annulus for liquid backflow around the outside of the tip to backwash the outside of the tip beyond the length that will be inserted into a liquid on the AL.

Wash buffer dispensed from the pipette tip at the wash station to cleanse the tip backflows vertically in annulus 277 and spills over into well 273, where it drains through drain 275 to a waste container below the worksurface in the AL. The wash station serves also as a waste disposal station. For waste disposal from the pipette tip without washing the tip, the tip is positioned over well 273 and the waste is dispensed to drain 275. For waste disposal it is not needed to position the tip in the fountain.

Figure 12:
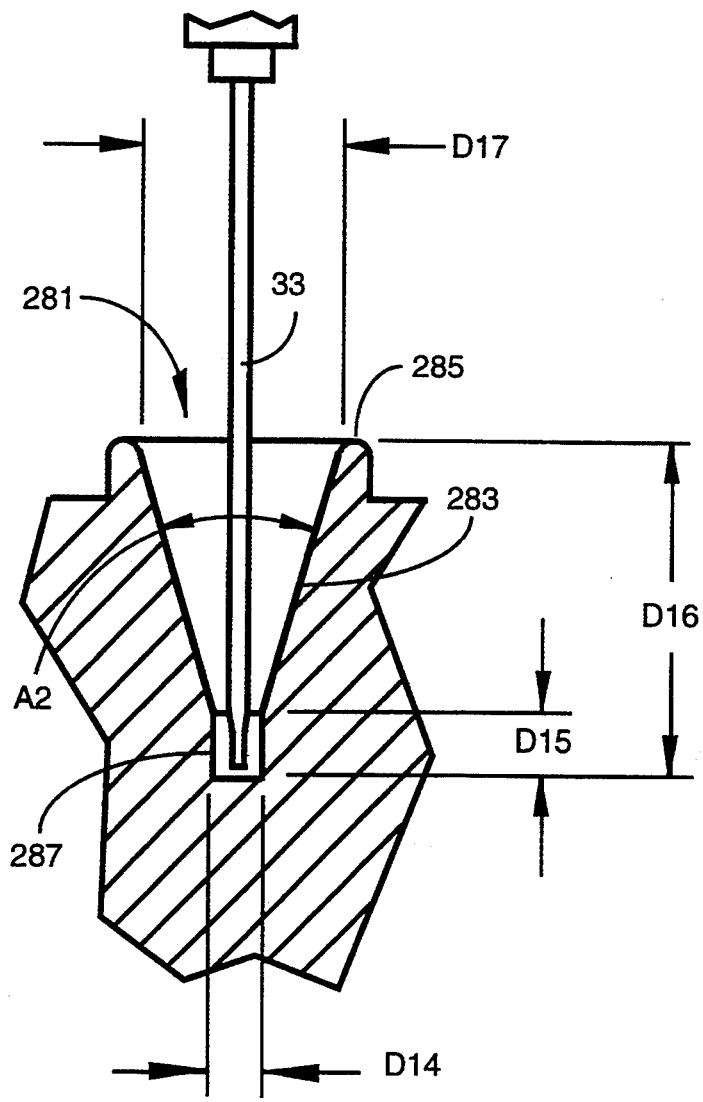
FIG. 12 shows a section through a container at an incubation station in a preferred embodiment, with a pipette tip inserted into the container cavity.

FIG. 12 is a section through one of the reaction vessels 281 at incubation station 21 with the pipette tip shown inserted into the vessel. The reaction vessel is machined with sloping sides such as side 283, a raised lip 285, and a cylindrical chamber 287. In the preferred embodiment the material for the plate is aluminum, for the desirable heat transfer characteristics, and the surface is coated with Paralene (TM) before use so the aluminum cannot react with the materials placed in the reaction volume. The Paralene coating is not shown in FIG. 12.

The raised lip is so the lid, which has a sheet of flexible material on the undersurface, butyl in the preferred embodiment, will seal to the reaction vessel when the lid is closed. Chamber 287 is where material is actually deposited and where reaction is accomplished.

The plate at station 21 into which the reaction vessels are machined is a replaceable modular unit, so plates can be assembled to the AL with reaction vessels of different sizes for different purposes. The vessel shown in FIG. 12 is for reaction volumes of about 50 micro-liters. Diameter D14 is about 1.25 mm and depth D15 is about 1.52 mm. Total depth D16 is about 8 mm, diameter D17 is about 6 mm, and angle A2 is about 40 degrees in the embodiment shown.

Material is deposited in chamber 287 for reaction, and removed from the chamber when reaction is complete. Before another reaction can be accomplished with possibly different materials entirely, the chamber has to be cleaned, which is accomplished in much the same manner as the cleaning of the pipette tip at station 25 described above. First a quantity of wash buffer is aspirated at storage station 30 (FIG. 1), then the pipette tip is moved to the reaction vessel as shown in FIG. 12. Wash buffer is dispensed into chamber 287 and backflows in the annulus between the tip and the wall of the chamber, similar to the action at the wash station. The volume above chamber 287 is large enough for a relatively large volume of buffer to be used in the process. After the washing action, the residue is piperted to waste at station 25. It has been determined in practice that the reaction chambers can be washed up to five times and reused before the plate at the incubation station has to be replaced to avoid contamination.

Appendix A—A Further Application Example

There is a great need for automation in molecular biology (1), but most workers have adapted general-purpose robotic devices to the need (2), with less than satisfactory results. This application example describes a commercially important procedure performed with apparatus according to the present invention, illustrating the utility of the invention. There are many other procedures that may be accomplished with the apparatus as described, or with minor modifications. Reference numbers are provided in parentheses throughout the example, and a reference list is provided at the end of the example to provide direction further background information.

Southern blotting, a very widely practiced technique in the molecular biology laboratory, is used to determine the length of DNA fragments homologous to a particular DNA probe (3). It has proven extremely valuable in tracking genetic diseases and identifying the presence of specific forms of genes in complex samples such as human genomic DNA (4, 5). The specific chemical steps required for Southern blotting (such as blotting transfer to membranes, membrane handling, and autoradiography) are not amenable to automation, though some attempts have been made (6). A novel chemistry has been developed which produces results equivalent to those from a Southern blot experiment; the process is solution based which allows for total automation by a liquid handling robot. The details of this chemistry are described elsewhere (7, 8). An essential difference between Southern blotting and this new approach is that the order of the electrophoretic size separation and hybridization are reversed. The new liquid-based methodology involves the following steps: 1) genomic DNA is simultaneously digested with a restriction enzyme and fluorescently labeled; 2) the genomic DNA is denatured and a biotin labeled probe is hybridized in solution to specific target molecules within the population of restricted genomic DNA fragments; 3) the specific hybrids are captured onto the surface of streptavidin functionalized papamagnetic particles while the remainder of the restricted genomic DNA population is not; 40 non-specific genomic DNA molecules in solution and bound to the particles are removed by stringent washing; 5) the captured hybrid/paramagnetic particle complexes are loaded directly into the well of a denaturing electrophoresis gel and the released labeled target molecules are detected when they electrophoreses past a laser scanned region a defined distance from the sample loading well; 6) collected fluorescent light is measured and the resultant data is analyzed. Other workers have described techniques where hybridization precedes electrophoresis but these techniques did not produce results where the length of the fragments analyzed could be correlated exactly to fragments in a Southern blot (9, 10).

The chemical methodology described above lends itself to automation with a robotic liquid handling system according to the present invention, and yields the information equivalent to that obtained from the Southern blotting technique. Automation of a DNA diagnostic application for sex typing using apparatus according to the invention is described, involving detection of a repeat sequence in the DYZI locus on the Y chromosome (11). The repeat unit length is 3.6 kb, and anywhere from tens to thousands of the repeat units may be present in tandem depending on the nature of the DNA sample. The usefulness of this Y-chromosome repeat detection for the clinical chemist lies in its ability to identify quickly the presence of male DNA in unknown samples. It can serve both as an initial screening before further expensive testing or simply as a positive control in forensic or X-linked genetic disease testing. A single Eco RI repeat from this genetic region has been cloned into a plasmid vector and used successfully as a hybridization probe to detect the presence of male DNA (12). Detection of this Y-chromosome repeat is typically done using the conventional Southern blotting procedure.

Reagents used in the Procedure

Human genomic DNA is extracted from either lymphocyte blood fraction (13) or two different harvested cell line cultures (Raji, black male; R562, Caucasian female; American Type Culture Collection, Rockville, Md. (14) using a model 340A Nucleic Acid Extractor (Applied Biosystems, Inc. (ABI), Foster City, Calif.). Extracted DNA is dissolved in 1 mL sterile deionized water and its concentration determined spectrophotometrically (1.0 A at 260 nm=50 micro-g/mL DNA). The DNA is diluted with sterile deionized water to a final concentration of 0.2 micro-g/micro-L.

Oligonucleotides are synthesized by the phosphoramidite approach (15) using a Model 381A DNA Synthesizer (ABI) at 0.2 micro-tool scale (16) with (2-O-cyanoethyl)-phosphoramidites (ABI). Crude ammonia hydrozylates are purified by Oligonucleotide Purification Cartridges TM (ABI) (17), evaporated to dryness, and stock solutions are prepared by dissolving in 1 mL sterile deionized water. Oligonucleotide concentration is determined spectrophotometrically from a dilution of the stock (1.0 A at 260 nm=33 micro-g/mL DNA).

The unlabeled oligonucleotide used for probe labelling ("Rsa I ligaid") has sequence 5' TCA ACA TCA TAA CIG AAA A 3' and is diluted to a final concentration of 25 pmol/micro-L. The unlabelled oligonucleotide used for target labelling (EcoRI ligaid") has the sequence 5' AAT TAC AAC ATC ATA ACT GAA AA 3' and is diluted to a final concentration of 5 pmole/micro-L.

A 60 base length oligonucleotide containing ten fluorescein molecules ("[F]60 mer") is prepared from the sequence 5' CTT TTC TTT TCT TTT CTT TTC TTT TCT TTT CTT TTC TTT TCT TTT CAG TTA TGA TGT TGT 3' and is used for target labelling. The unlabeled oligonucleotide is reacted with metabisulfite/EDTA to modify citosine residues for attachment with 6-M ethyl-fluorescein-N-hydroxysuccinimide ester (18). The product is HPLC purified and its concentration determined spectrophotometrically by a ratio of dye to DNA absorption (19).

A biotin labelled oligonucleotide ("[B]30 mer") is used for probe labelling. It is synthesized in the same fashion as described above with the sequence 5" TXX XTT TTT TTT TTT TTA GTT ATG ATG TTG T 3' where X represents modified cytosine residues which contain an amino linker arm (Molecular Biosystems, San Diego, Calif.). After purification and quantitation, the oligonucleotide is reacted with biotin-N-hydroxysuccinimide ester (Pierce, Rockford, Ill.) and purified by HPLC in a manner analogous to the fluorescent labelled oligonucleotide above.

Denaturation reagent is prepared just prior to use by mixing together 6 parts of reagent $D_a$ plus one part of reagent $D_b$. Reagent $D_a$ is composed of 200 mmol/L sodium hydroxide, and 800 mmol/L sodium carbonate. Reagent $D_b$ is composed of 12.9% sodium polyacrylate, 5.85 mol/L sodium perchlorate, 10 mmol/L trisodium-EDTA, and is prepared by combining 18 mL (24.2 g) of stock sodium polyacrylate, 39 mL (64.4 g) of 9 mol/L sodium perchlorate (Aldrich Chemical Co., Milwaukee, Wis.; #20,842-6), and 3 mL of stock trisodium-EDTA. Stock (43%) sodium polyacrylate is prepared by slow addition (Caution!—Heat evolved) of 50% NaOH (wt/wt) to 250 g. polyacrylic acid (Aldrich #19,202-31 until a 1:100 dilution of a 100 micro-L aliquot is pH 8.0. Stock (200 mmol/L) trisodium-EDTA is prepared by dissolving 74.4 g. (0.2 moles) disodium EDTA (International Biotechnology Inc., New Haven, Conn.; #70182) in 900 mL deionized water and titrating with 50% NaOH (wt/wt, approx. 10 mL) to pH 8.0 and then diluting to a total volume of 1 L with aleionized water.

Three buffer solutions are used to wash paramagnetic particles and their composition is as follows: buffer A=1.0 X SSPE (180 mmol/L sodium chloride, 10 mmol/L monobasic sodium phosphate ptt 7.4, 1 mmol/L EDTA), 0.5% Tween-20 (Aldrich; #27,434-8); buffer B=118 mmol/L sodium chloride, 16.5 mmol/L sodium carbonate, 7.8 mmol/L sodium bicarbonate, 0.5% Tween-20; buffer C=100 mmol/L sodium chloride.

Streptavidin functionalized magnetic particles [Magnetic Streptavidin 446D, Advanced Magnetics Inc. (AMI), Cambridge, Ma. ] are pre-washed twice before use at 23 degrees C. using buffer A. A 1.5 mL microtube containing a measured aliquot of magnetic particles is first placed directly against a BioMag Separator TM (AMI) containing rare-earth magnets to draw all the particles to the tube's wall. The supernatant is removed from the separated particles and replaced with 500 micro-L of buffer A. The solution is vortexed vigorously to ensure complete resuspension of the particles. Another cycle of separation and resuspension with buffer A is performed. Finally the suspension is separated, the supernatant is discarded and the particles resuspended in a volume of buffer A equivalent to the original aliquot.

Procedures

Both probe and target DNA are labelled by the covalent attachment of a derivatized oligonucleotide to restricted plasmid or genomic DNA respectively. This simultaneous restriction/ligation technique has been previously described (20, 21). Probe labelling is performed manually as follows. A 100 micro-L reaction volume is prepared containing a i mmol/L ATP (Sigma Chemical Co., St. Louis, Mo. #A-0770), 15 mmol/L dithiothreitol (Sigma, D-9779), 1 X restriction enzyme buffer (Promega Corp., Madison, Wis.), 50 micro-g/mL BSA-OAc (Promega), 10 micro-g pY3,4 plasmid DNA, 60 U Rsa I restriction enzyme (all enzymes used are from Promega), 10 U $T_4$ DNA ligase, and 69 pmol each of the [B]30mer labelled oligonucleotide and the Rsa I ligaid. Enzyme amounts used are based on units of enzyme activity per weight of DNA, using 6 U/micro-g.

[B]30mer label and Rsa I ligaid amounts used are based on 2.5X stochiometric excess of each oligonucleotide over moles of single-strand (ss) "ends" produced by restriction plasmid probe. The reaction product (0.1 micro-g/micro-L, 276 fmol ss ends/micro-L) is diluted to 160 fmol ss ends/micro-L with sterile deionized water.

Target labelling, denaturation and hybridization, capture, and magnetic particle washing are performed automatically by the apparatus. For target labelling, a 50 micro-L aliquot of sample genomic DNA is first prerestricted for 2 hr at 37 degrees C. in a total reaction volume of 65.5 micro-L by addition of 6.5 micro-L 10X restriction enzyme buffer, and 40 U Eco RI restriction enzyme. All restriction fragments produced are then labelled by incubation for 2 hr at 37 degrees C. in a total reaction volume of 100 micro-L containing 1 mmol/L ATP, 1X restriction enzyme buffer, 60 U EcoRI restriction enzyme, 25 pmol [F]60 mer, 25 pmol EcoRI Ligaid, and 10 U T4 DNA Ligase. Labelled genomic DNA is denatured and hybridized with the Y-chromosome repeat specific probe by addition of 60 micro-L denaturation reagent and 1.6 pmol of biotin labelled probe in 10 micro-L, heated to 93 degrees C. for 15 min., cooled to 48 degrees C. for 30 min., and then cooled to 37 degrees C. Specific hybrids and excess biotin labelled probe are captured onto solid phase by addition of 40 micro-L of streptavidin-paramagnetic particles with mixing and allowed to incubate at 37 degrees C. for 10 min. Three successive washing cycles of 1) magnetic separation, 2) removal of supernate (decantation), and 3) replenishment and incubation at 53 degrees C. for 2 min. with buffer B are performed, followed by one cycle with buffer C at 23 degrees C. After a final magnetic separation and decantation, the particles are heated at 42 degrees C. for 15 min. to evaporate residual fluid, then maintained at 23 degrees C. until ready to load into an electrophoresis gel.

To prepare a denaturing agarose gel, 1.07 g. agarose (Biorad, Richmond, Calif.; High Strength Analytical Grade #162-01261, 0.33 g. Ficoll (Sigma, #2637) and 133 mL aleionized water are placed in a tared flask and boiled until the agarose is dissolved. Enough additional deionized water is added to the flask to return it to its tared weight before boiling to compensate for evaporative loss. The agarose solution is cooled to 40 degrees C. by placing intermittently on ice with constant swirling, 1.33 mL of 100X Studier Buffer (3 mol/L NaOH, 100 mmol/L EDTA) is added, the solution is then cooled to 30 degrees C. and poured into a glass bottom gel tray (22×28 cm.) and a well-forming combing introduced into the gel. 1.2 L of 1 X Studier Buffer is pored to cover the gel once solidified.

A 2 X stock electrophoresis loading buffer 2 X LB) is prepared from equal volumes of 10 X Studier Buffer (300 mmol/L NaOH, 10 mmol/L EDTA), I mg./mL Dextran Sulfate (Sigma Chemical Co., St, Louis, Mo., #D-8906), and 15% Ficoll (Sigma, F2637).

Fluorescent internal fane size standards are also prepared by the simultaneous restriction/ligation of commonly available DNAs (i.e., lambda. phage, phiX174 virus, or pBR322 plasmid) by methods identical to those described for target labelling, except that the "label" oligonucleotide is derivitized with the dye "JOE" (22') which fluoresces at a longer wavelength than fluorescein and can be discriminated spectroscopically by the fluorescent scanner. A typical preparation is "[JJ]lambda+pBR(HindIII), a JOE labelled combination of Lambda and pBR 322 DNAs restricted with Hind III. In a total volume of 100 micro-L are combined 10 micro-g. of lambda DNA, 0.9 micro-g. of pBR322-plasmid DNA, 25 pmol [j]60mer (a molecule analogous to [F]60 mer but labelled with JOE) and all other reagents as indicated above for target labelling. The reaction product (3.2 fmol double-stranded fragments/micro-L) is diluted to 400 amol/micro-L for use.

Dried magnetic particles are resuspended in 6 micro-L of an equal volume mixture of size standard and 2 X LB prior to loading into an electrophoresis gel.

Apparatus

The main mechanical mechanism is a three-axis cartesian robot. At the end of its "arm" (z-axis) is placed a fixed metallic syringe needle which performs all necessary fluid aspiration and dispensation steps. System plumbing comprises two syringe pumps (250 micro-L and 2.5 micro-L) drawing from a common 1 L sterile deionized reservoir. Effluent from both syringes is directed through a narrow diameter tube to the end of the XYZ arm.

On the work surface, a cold storage (4 degrees C) compartment provides a stable environment for enzymes and probes for up to several days. A temperature regulated rack for incubations allows 96 samples to be labelled simultaneously. Another temperature regulated station houses a motor-controlled rare-earth bar magnet which can separate particles from 24 samples in a batch fashion. There are also defined positions for twelve 1.5 mL microfuge tubes of reagent, two 35 mL bottles of buffer, five 100 mL bottles of temperature regulated buffer, a rack of 1.2 mL microfuge tube of sample DNA, and a needle tip wash station.

A Macintosh II ™ computer (Apple Computer, Inc., Cupertino, Calif.) provides the user interface for both the robotic and separate scanner instruments. The robotic instrument's operations are programmed and controlled through an ironic language where pictorial representations are used to describe chemical processes (24). This approach allows easy programming and editing and is quick to learn. The syntax of the programming language is inherent in its structure.

The robotic instrument performs all the operations necessary to perform target labelling, solution hybridization, solid phase capture and parsmagnetic particle wash steps. Before automatic operation begins, the work surface is first manually loaded with all the necessary reagents, disposable reaction tubes and sample genomic DNA (target). The instrument begins operation by first distributing an aliquot from each DNA sample tube into a corresponding tube position within the incubation rack for labelling. By addition of necessary reagents, each target sample is then simultaneously restricted and fluorescently labelled. Each sample plus an aliquot of denaturant and probe is then transferred to the magnetic separation station where a defined temperature profile is executed to perform denaturization and hybridization. Streptavidin parsmagnetic particles are added to each sample to capture specific hybrids, and finally, the parsmagnetic particles are washed several times with a series of buffers and prepared for loading onto the fluorescent scanner.

For detection of the chemical product produced by the robotic instrument, samples are manually loaded into gel wells in submarine fashion and electrophoresed at 4.5 volts/cm (325 milliamps) for 4 to 7 hours with buffer circulation. A 370A Sequencer (ABI) modified to accept horizontal agarose gels is used to detect migrating fluorescent molecules (25). Real-time detection is accomplished by the use of laser excitation and fluorescent detection optics which scan across the gel's width, typically at a distance of 4.0 cm. from the sample wells (22). Data analysis software allows for quantitative interpretation of electrophoresis data. The data can be displayed in the form of a "gel view" which presents a record of all the fluorescent molecules which have passed through the scan region. This gel view appears to be a photograph of the gel, but time, rather than position is along the direction of electrophoresis. Alternatively, data can be displayed in a chromatographic view, which is a history of the fluorescence in a particular gel lane that passes through the scan region. The chromatographic view is an analog to the kind of data presented by a densitometer.

Results and Discussion

The robot's physical performance was evaluated in a number of ways to verify proper function of temperature regulation systems and to validate liquid handling precision and accuracy. Temperature profiles at all relevant places on the worksurface were measured. Temperatures (4-100 degrees C) achieved were reproducible. No discernable deviation or drift in the temperature of tube contents was detectable with the thermocouple arrangement used which has a resolution of 0.1 degree C. Accuracy of piperting (1-100 micro-L) has been measured both spectrophotometrically and gravimetrically and typically found to be within 1-5% depending upon sample viscosity with a Cv of 1.0% at 1.0 micro-L (data not shown).

The use of a single piperting tip required a study of cross-contamination. Contamination resulting from carryover from one reagent tube to the next when a multiple aspiration is performed was measured spectrophotometrically to be 0.5 micro-L. Sample-to-sample cross contamination after probe tip washing is undetectable as previously reported by other workers in a similar liquid handling instrument (26). Reagent pollution due to multiple aspiration without tip washing occurs at two places in the entire process as currently practiced. The first opportunity for potential cross-contamination is in the mixing of common restriction and labelling reagents ("palerting") where the potential exists for ATP to contaminate buffer, buffer to contaminate restriction enzyme, and so forth. This poses little threat to reagent integrity since the order in which reagents are aspirated can be judiciously chosen so as to accommodate a slight amount of carry-over. Furthermore, this operation occurs only once during execution of the entire process. The second occurrence of carry-over due to multiple aspiration is when sample DNA is transferred from the labelling station to the magnetic separation station. Here a small amount of denaturant may contaminate the probe reagent. Probe reagent could be multi-dispensed to each tube position within the magnetic separation station before transfer of labelled DNA to alleviate this problem.

Electrophoretic detection produces, after data analysis, both a reconstructed representation of a "gel" and a chromatogram view through an electrophoresis lane. A major band at 3.6 kb represents detection of hybridization to multiple copies of the Y chromosome repeat unit. The profile describes measure of relative fluorescence (Y-axis) as a function of arrival time at the detector of migrating species (X-axis). Arrival time can be related to molecular size since the electrophoresis gel material produces a separation based on size. Analogous to a Southern blot experiment, observed results thus give information of amount and molecular size of a DNA fragment with a sequence complementary to a given probe.

Good signal uniformity (Cv=12%) was observed from the result of pY3.4 probe hybridization with five identical DNA samples.

A control experiment was done where five different DNA samples were hybridized with either the Y chromosome repeat probe or a probe which is not homologous to the human genome (plasmid pSP64 labelled in the same manner as described above). Varying signal intensity was observed within the group of male DNA's. As previously reported by Lua (12) we observed that the DNA sample of Black origin exhibited a stronger signal, and the DNA sample of Asian origin exhibited a weaker signal than the DNA sample of Caucasian origin. Also as noted in the literature, secondary hybridization to smaller size fragments was observed even in the female DNA. No hybridization with the non-homologous probe was detected in any of the human DNA samples.

The system was able to produce consistent experimental results from 24 DNA samples in 10.5 hours of elapsed time from loading samples and reagents on the robot to receiving analyzed data from the scanner. The robotic instrument was routinely loaded with reagents and samples toward the end of a work day and operated overnight (actual operating time of 6.5 h). The next morning particle suspensions were loaded onto the scanner instrument for electrophoresis and detection and resultant data was analyzed (4 h). The actual hands-on-time by an operator was less than two hours and required only placement of reagent tubes in holes, gel preparation and loading, and computer interaction. This system can then provide genetic information from a DNA sample overnight as compared to typically days than is currently available with manual Southern blotting.

Example Summary and Conclusions

From the example above it is concluded that a robotic liquid handling instrument according to the invention can be used successfully to automate specific human gene detection in such a way to yield the equivalent experimental result to that produced by Southern blotting. The manner in which this result is accomplished is simpler and faster than the manual methods typically employed. The individual liquid handling steps are executed with precision. Since operation is computer controlled the process can be performed consistently, reliably, and relentlessly providing a new opportunity for high sample throughput.

The MAcintosh II ™ controller of the robot and scanner instruments have been interfaced to an Ethertalk ™ network and have allowed sending both process control code and resulting data between workers.

The continued development of automated DNA sequencing using a robot similar to the one described herein has recently been discussed in another document (25). The robot's unique combination of attributes (accurate piperting, XYZ motion, temperature control and magnetic particle handling make it ideally suited to perform this and many other chemical methodologies.

References for Appendix A (1) Landergren U, Kaiser R, Caskey C, Hood L. DNA diagnostics—molecular techniques and automation. Science 1988; 242:229-37.
(2) Wilson R K, Yuen A S, Clark S M, Spence C, Arakelain P, Jood L E. Automation of dideoxynucleotide DNA sequencing reactions using a robotic workstation. Biotechniques 1988; 6:776-87.
(3) Southern, E M. Detection of specific sequences among DNA fragments separated by gel. J Mol Biol 1975; 98,3:503-17
(4) Caskey T C. Disease diagnosis by recombinant DNA methods. Science 1987; 236:1223-28.
(5) Watkins P C. Restriction fragment length polymorphism (RFLP): applications in human chromosome mapping and genetic disease research. Biotechniques 1988; 6,4:310-19.
(6) Getsten D M, Zapolski E J, Golab T J, Buas M, Ledley R S. Computer controlled DNA electrophoresis and hybridization. Proc. Meet Int. Electrophor. Soc. 1986; 5:187-90.
(7) Kieth D, Hoff L B, Mayrand P E, McBride L J, Robertson J, Recknor M, Ziegel J, Meister S, Whitley N, Kronick M. Detection and sizing of fluorescently labelled DNA fragments following in-solution hybridization: an alternative to traditional Southern blotting. Manuscript submitted to Nuc. Acids Res.
(8) Kronick M N, Kieth D H, McBride L J, Whitley N M, Hunkapiller M W. Method and kit for detecting a nucleic acid sequence. Eur. patent appl. no. 0322311, 1988.
(9) Gainper H B, Cimino G B, Isaacs S T, Ferguson M, Hearst J. Nuc. Reverse Southern hybridization. Nuc. Acids Res. 1986; 14:9943-9954.
(10) Jones F S, Grimberg J I, Fischer S G, Ford J P. Detection of sickle-cell mutation by electrophoresis of partial RNA:DNA. Gene 1985; 39,1:77-83.
(11) Bostock C J, Gosden J R, Mitchell A R. Localisation of malespecific DNA fragment to subregion of the human Y chromosome. Nature 1978; 272:324-328.
(12) Lau Y, Schonberg S. A male-specific DNA probe detects heterochromatin sequences in a familial Yq⁻ chromosome. Am. J. Hum. Genet. 1984; 36:1394-96.
(13) Lymphocyte preparation II. ABI 340A Nucleic Acid Extractor User Manual 1989; 3:12.
(14) Cell culture preparation. ABI Nucleic Acid Extractor User Manual 1989; 3:10.
(15) Caruthers M H, Barone A D, Beaucage S L, et al. Chemical synthesis of deoxynucleotides by the phosphoramidite approach. Methods Enzymol 1987: 154:287-313.
(16) ABI 370A User Bulletin 1986; 3:7.
(17) McBride L J, MsCollum C, Davidson S, Efcavitch J W, Andrus A, Lombardi S J. A new, reliable cartridge for the rapid purification of synthetic DNA. Biotechniques 1988; 6:362-7.
(18) Draper D and LE Gold. A method for linking fluorescent labels to polynucleotides: application to studies of ribosomeribonucleic acid interactions. Biochemistry 1980; 19,9:1774-81.
(19) ABI 370A User Bulletin 1989; 11.
(20) Kieth D H, Kronick M R, McBride L J, Whitley N M. Labelling by simultaneous ligation and restriction. Eur. patent appl. no. 0327-429, 1989.
(21) Carrano A V, Lamerdin J, Ashworth L K. A high-resolution, fluorescence-based, semiautomated method for DNA fingerprinting. Genomics 1989; 4:129–136.
(22) Fung S, Woo S L, Menchen S M, Connel C R, Heiner C. Method of detecting electrophoretically separated oligonucleotides. Eur. patent appl. no. 0233053, 1986.
(23) Shigeura J. Mechanical Design of Small-Volume Fluid-Handling Robots for the Molecular Biology Laboratory. Proc. 5th International Symposium on Laboratory Robotics 1989.
(24) Guiremand H. Popframes programming interface. Eur. patent appl. no. 00000-00000.
(25) Connell C, Fung S, Heiner C. Automated DNA sequence analysis. Biotechniques 1987; 5:342–348.
(26) Severns M L, Brennan J E, Kline L M, Eply K M. Pipette cleaning in automated systems. J. Automatic Chemistry 1986; 8,3:135–141.
(27) Chem. Eng. News 1989; Nov 13:6.

It will be apparent to a worker skilled in the art that there are many changes that can be made in the details of the invention as described without departing in any significant degree from the spirit and scope of the invention. For example, the numbers of positions at the various stations need not be as shown in the preferred embodiments. More or fewer positions could be used. As another example, the dimensions and construction details can vary widely. There are many ways to accomplish the resolution needed for the robot, and many different, kinds of sensors and drives that can be used. As still another example, there are many different materials that would be suitable for different parts of the apparatus, such as the plate at the incubation station, and the material described is the preferred mode. Many such changes in detail can be made without departing from the spirit and scope of the invention.

What is claimed is:

1. A liquid-handling instrument for transferring liquid from one container to another comprising:
    a stationary worksurface having machined registration elements for accurately locating and supporting a modular container station for holding said containers of liquid;
    a pipette subsystem for aspirating and dispensing liquid, said pipette subsystem comprising a pipette tip coupled to a capacitance sensor;
    a robotic translation subsystem for moving said pipette tip to all containers on said worksurface and into and out of said containers;
    a gauge block securely fastened to and accurately positioned on said worksurface relative to said registration elements, and having surfaces substantially orthogonal to directions of movement of said pipette tip by said robotic translation subsystem; and
    a control subsystem for automatically managing said liquid transfers;
    wherein said control subsystem controls said robotic translation subsystem to move said pipette tip to each of said surfaces on said gauge block wherein the pipette tip and the capacitance sensor sense the position of the machined surface of said gauge block thereby establishing a home position on said worksurface for said liquid transfers.

2. An instrument as in claim 1 wherein said registration elements comprise a cavity for positioning the modular container station, said cavity positioned accurately relative to said gauge block, such that a first modular station may be removed and a second modular station substituted therefor while maintaining known dimensions from containers in said stations to the known position of said gauge block.

3. An instrument as in claim 1 wherein said pipette subsystem further comprises a first syringe pump operable by said control subsystem at a first rate for aspirating and dispensing liquids with a first degree of accuracy and a second syringe pump operable by said control subsystem at a second rate for aspirating and delivering liquids with a second degree of accuracy, said first and second syringe pumps being commonly connected to said pipette tip.

4. An instrument as in claim 1 wherein said robotic translation subsystem comprises a robot having a carriage over said stationary worksurface for carrying said pipette tip, said carriage being translatable over the area of said worksurface and also translatable toward and away from said worksurface.

5. An instrument as in claim 4 wherein said robot is a cartesian robot having three directions of travel, two in a horizontal plane and the third direction vertical.

6. An instrument as in claim 5 wherein said robot has three principal drives, and said drives are powered by electric motors.

7. An instrument as in claim 1 wherein said control subsystem comprises an iconic interface having user-selectable icons for programming a protocol and for entering values for control variables, said icons representing specific steps in said protocol and arrangeable in series to determine action sequences, said icons being expandable-in-place to show other steps that an icon comprises.

8. An instrument as in claim 1 further comprising a tip washing station located on said stationary worksurface, and said tip washing station comprises;
    a fountain for enclosing said pipette tip during washing; and
    a well surrounding said fountain such that liquid flowing from said fountain flows into said well, said well having a drain disposed to communicate unwanted material to an external location.

9. An instrument as in claim 1 wherein at least one of said containers supported by said worksurface comprises closure means having a flexible duck-billed portion extending toward the interior of said container.

10. An instrument as in claim 9 wherein said container comprises an upper rim and said closure means comprises an annular cavity portion surrounding said duck-billed portion for sealing to said upper rim.

11. An automated laboratory for transferring liquids from one container to another and performing a chemistry protocol comprising:
    a stationary worksurface having machined registration elements are accurately locating and supporting a modular container station for holding said containers of liquid;
    a pipette subsystem for aspirating and dispensing liquid, said pipette subsystem comprising a pipette tip coupled to a capacitance sensor;
    a robotic translation subsystem for moving said pipette tip to all containers on said worksurface and into and out of said containers;
    a heating subsystem for heating liquids in said containers;
    a cooling subsystem for cooling liquids in said containers;
    a gauge block securely fastened to and accurately positioned on said worksurface and having surfaces substantially orthogonal to directions of movement of said pipette tip by said robotic translation subsystem; and a control subsystem for automatically managing said chemistry protocol;

wherein said control subsystem controls said robotic translation subsystem to move said pipette tip to each of said surfaces on said gauge block wherein the pipette tip and the capacitance sensor sense the position of the machined surface of said gauge block thereby establishing a home position on said worksurface for said liquid transfers.

12. An automated laboratory as in claim 11 further comprising an incubation station heatable by said heating subsystem and coolable by said cooling subsystem, said incubation station having cavities coated with a chemically inert coating, and a latching lid with a sealing surface such that with said lid closed and latched, said cavities are individually sealed.

13. An automated laboratory as in claim 12 wherein said cavities each have a machined upper lip such that force exerted on said lid by latching said lid is concentrated on said machined upper lips of said cavities to facilitate sealing.

14. An automated laboratory as in claim 12 wherein said cavities are machined into a metal block, and said metal block is securely fastened to and accurately positioned on said worksurface and removable, such that a block of cavities may be removed and replaced with a new block of cavities.

15. An automated laboratory as in claim 12 wherein said cavities have a lower cylindrical portion for holding a sample and an upper conical portion to provide additional volume to hold liquid aspirated during a cleaning procedure.

16. An automated laboratory as in claim 11 further comprising a magnetic system for passing a magnetic field through containers supported by said worksurface to separate paramagnetic particles from a liquid in said containers, said magnetic system comprising a station having two rows of containers for holding liquid, and a magnetic bar supported on an elevator such that said magnetic bar may be selectively elevated and withdrawn from between said rows of containers.

17. An automated laboratory as in claim 16 wherein said magnetic bar comprises rare-earth magnetic material.

18. An automated laboratory as in claim 11 wherein said registration elements comprise a cavity for positioning the modular container station, said cavity positioned accurately relative to said gauge block, such that a first modular station may be removed and a second modular station substituted therefor while maintaining known dimensions from containers in said stations to the known position of said gauge block.

19. An automated laboratory as in claim 11 wherein said pipette subsystem further comprises a first syringe pump operable by said control subsystem at a first rate for aspirating and dispensing liquids with a first degree of accuracy and a second syringe pump operable by said control subsystem at a second rate for aspirating and delivering liquids with a second degree of accuracy, said first and second syringe pumps being commonly connected to said pipette tip.

20. An automated laboratory as in claim 11 wherein said robotic translation subsystem comprises a robot having a carriage over said stationary worksurface for carrying said pipette tip, said carriage being translatable over the area of said worksurface and also translatable toward and away from said worksurface.

21. An automated laboratory as in claim 20 wherein said robot is a cartesian robot having three directions of travel, two in a horizontal plane and the third direction vertical.

22. An automated laboratory as in claim 21 wherein said robot has three principal drives, one for each of said three directions of travel, and said drives are powered by electric motors.

23. An automated laboratory as in claim 11 wherein said control subsystem comprises an iconic interface having user-selectable icons for programming a protocol and for entering values For control variables, said icons representing specific steps in said protocol and arrangeable in series to determine action sequences, said icons being expandable-in-place to show other steps that comprise art icon.

24. An automated laboratory as in claim 11 further comprising a tip-washing station located on said stationary worksurface, and said tip-washing station comprises;

a fountain for enclosing said pipette tip during washing; and a well surrounding said fountain such that liquid flowing from said fountain flows into said well, said well having a drain disposed to communicate unwanted material to an external location.

25. An automated laboratory as in claim 11 wherein at least one of said containers supported by said worksurface comprises closure means having a flexible duckbilled portion extending toward the interior of said container.

26. An automated laboratory as in claim 25 wherein said container comprises an upper rim and said closure means comprises an annular cavity portion surrounding said duck-billed portion for sealing to said upper rim.

27. An automated laboratory as in claim 11 wherein said control subsystem comprises control routines with steps for performing automated specific gene detection.

28. An automated laboratory in claim 11 wherein said control subsystem comprises control routines with steps for performing automated nucleic acid sequence detection.

29. An automated laboratory in claim 11 wherein said control subsystem comprises control routines with steps for performing automated fluorescent labelling of nucleic acids.

30. A method for transferring liquid by a robotic translation system from a first container holding a first volume of liquid to a second container holding a second volume of liquid comprising steps of:

aspirating a third volume of liquid from said first volume of liquid in said first container with a pipette having a pipette tip and a capacitance sensor for sensing the position of said pipette tip relative to proximate surfaces;

moving said pipette tip away from said first container by action of said robotic translation system;

dispensing a first droplet of liquid from said pipette tip such that said first droplet depends from said pipette tip but does not separate therefrom, said first droplet having a known droplet volume;

moving said first droplet with said pipette tip by said robotic translation system until said first droplet touches the surface of said second volume of liquid, stopping translation when said capacitance sensor signals contact, and allowing said first droplet to become confluent with said second volume of liquid;

withdrawing said pipette tip from said second volume of liquid;

dispensing a second droplet of liquid from said pipette tip such that said second droplet of liquid depends from said pipette tip but does not separate therefrom, said second droplet having a volume equal to the volume of said first droplet;

moving said second droplet with said pipette tip by said robotic translation system until said second droplet touches the surface of said second volume of liquid, stopping translation when said capacitance sensor signals contact, and allowing said second droplet to become confluent with said second volume of liquid; and repeating the steps of dispensing droplets and transferring the droplets to said second volume of liquid until a predetermined volume of liquid is dispensed and transferred to said second volume of liquid.

31. A method for checking for positions of elements on a worksurface in a liquid-handling instrument having a pipette subsystem, said pipette subsystem comprising a pipette tip coupled to a capacitance sensor for sensing position of said pipette tip relative to proximate surfaces, said pipette tip movable over said worksurface by a robotic translation subsystem, said method comprising the steps of:

moving said pipette tip in a pattern and at a height over said worksurface such that said pipette tip will not contact any surface if every part is in its proper place;

stopping translation of said pipette tip if said pipette tip contacts any surface as signalled by said capacitance sensor; and activating a signal that a part is out of position.

32. A method for mixing liquids in a liquid handling instrument having a pipette subsystem with a pipette tip movable over a worksurface by a robotic translation subsystem, said method comprising the steps of:

moving said pipette tip by said robotic translation subsystem to immerse said pipette tip in a volume of liquid in a container;

aspirating liquid into said pipette ending with said pipette tip immersed in said volume of liquid in said container;

dispensing said aspirated liquid into said container while moving said pipette tip in a pattern encompassing substantially the space occupied by said volume of liquid in said con ruiner; and repeating the steps of aspirating and dispensing while moving said tip in said pattern to thoroughly mix the contents in said container.

* * * * *